(12) United States Patent
Basilion

(10) Patent No.: US 11,975,074 B2
(45) Date of Patent: May 7, 2024

(54) PHOTODYNAMIC THERAPY COMPOSITION

(71) Applicant: CASE WESTERN RESERVE UNIVERSITY, Cleveland, OH (US)

(72) Inventor: James Basilion, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 437 days.

(21) Appl. No.: 16/901,874

(22) Filed: Jun. 15, 2020

(65) Prior Publication Data

US 2021/0060170 A1 Mar. 4, 2021

Related U.S. Application Data

(63) Continuation-in-part of application No. 16/279,326, filed on Feb. 19, 2019, now Pat. No. 10,709,794, which is a continuation of application No. 15/629,281, filed on Jun. 21, 2017, now Pat. No. 10,207,005, which is a continuation-in-part of application No. 14/767,984, filed as application No. PCT/US2014/016932 on Feb. 18, 2014, now Pat. No. 9,889,199.

(60) Provisional application No. 62/861,802, filed on Jun. 14, 2019, provisional application No. 61/765,346, filed on Feb. 15, 2013.

(51) Int. Cl.
| | |
|---|---|
| A61K 47/64 | (2017.01) |
| A61K 31/695 | (2006.01) |
| A61K 41/00 | (2020.01) |
| A61K 49/00 | (2006.01) |

(52) U.S. Cl.
CPC ............ *A61K 47/64* (2017.08); *A61K 31/695* (2013.01); *A61K 41/0071* (2013.01); *A61K 47/645* (2017.08); *A61K 49/0036* (2013.01); *A61K 49/0056* (2013.01)

(58) Field of Classification Search
CPC ...... A61K 47/00; A61K 47/64; A61K 47/645; A61K 47/542; A61K 31/00; A61K 31/695; A61K 41/00; A61K 41/0071; A61K 49/00; A61K 49/0036; A61K 49/0052; A61K 49/0056
USPC ............... 424/1.11, 1.65, 9.1, 9.2, 9.6, 1.69; 514/330
See application file for complete search history.

(56) References Cited

U.S. PATENT DOCUMENTS

| | | | |
|---|---|---|---|
| 9,889,199 B2 * | 2/2018 | Basilion | A61K 47/60 |
| 10,207,005 B2 * | 2/2019 | Basilion | A61K 31/695 |
| 10,363,313 B2 | 7/2019 | Basilion | |
| 10,709,794 B2 * | 7/2020 | Basilion | A61K 49/0036 |
| 2008/0193381 A1 | 8/2008 | Babich et al. | |
| 2009/0061010 A1 | 3/2009 | Zale et al. | |
| 2010/0324008 A1 | 12/2010 | Low et al. | |
| 2012/0323164 A1 | 12/2012 | Kenney et al. | |

FOREIGN PATENT DOCUMENTS

| | | |
|---|---|---|
| WO | 2008/057437 A1 | 5/2008 |
| WO | 2011/106639 A1 | 9/2011 |
| WO | 2012/016713 A2 | 2/2012 |

OTHER PUBLICATIONS

Yao et al, Bioorganic & Medicinal Chemistry, vol. 28, No. 115319, pp. 1-14. (Year: 2020).*
Boinapally et al, Scientific Reports, vol. 11, No. 7114, 10 pages. (Year: 2021).*
Extended Search Report for Application No. 14751113.3-1453/ 2958596, dated Oct. 10, 2016.
Kularatne, Sumith A., et al., "Synthesis and Biological Analysis of Prostate-Specific Membrane Antigen-Targeted Anticancer Prodrugs", Journal of Medicinal Chemistry, vol. 53, No. 21, Nov. 11, 2010, pp. 7767-7777, KP055103918.
Ikeda, Masato, et al., "Supramolecular hydrogel capsule showing prostate specific antigen-responsive function for :; ensing and targeting prostate cancer cells", Chem. Sci., 2010, 1, 491-498.
EP Office action for Application No. 14751113.3-1109, dated Jan. 1, 2019.
U.S. Appl. No. 16/573,570, filed Sep. 17, 2019, U.S. Non-Final Rejection dated Jun. 10, 2022, 24 pgs.

* cited by examiner

*Primary Examiner* — D. L. Jones
(74) *Attorney, Agent, or Firm* — TAROLLI, SUNDHEIM, COVELL & TUMMINO, LLP

(57) ABSTRACT

A method of treating a PSMA expressing cancer in a subject includes (a) administering to the subject a PSMA-targeted phthalocyanine conjugate compound having the formula (I), (b) detecting the PSMA-targeted phthalocyanine compound bound to and/or complexed with the prostate cancer cells to determine the location and/or distribution of the prostate cancer cells in the subject, (c) surgical resection of the detected cancer, and (d) irradiating the PSMA-targeted phthalocyanine compound at the site of surgical resection, thereby inducing the cytotoxic effects of the phthalocyanine compound on residual prostate cancer cells following surgical resection.

27 Claims, 9 Drawing Sheets

PHOTODYNAMIC THERAPY COMPOSITION

RELATED APPLICATION

This application is a CIP of U.S. Ser. No. 16/279,326, filed Feb. 19, 2019, which is a Continuation of U.S. Ser. No. 15/629,281, filed Jun. 21, 2017, (now U.S. Pat. No. 10,207,005), which is a Continuation-in-Part of U.S. Ser. No. 14/767,984, filed Aug. 14, 2015, (Now U.S. Pat. No. 9,889,199), which is a National Phase of PCT/US2014/016932, filed Feb. 18, 2014, which claims priority to U.S. Provisional Application Ser. No. 61/765,346, filed Feb. 15, 2013. This application also claims priority from U.S. Provisional Application No. 62/861,802, filed Jun. 14, 2019, the subject matter of which are incorporated herein by reference in their entirety.

GOVERNMENT FUNDING

This invention was made with government support under Grant No. R01EB12099, awarded by The National Institutes of Health. The United States government has certain rights in the invention.

TECHNICAL FIELD

This application relates to methods and therapeutic compositions for the treatment and detection of cancer, and more particularly relates to methods combining image guided surgery and photodynamic therapy including the use of targeted photodynamic therapeutic compositions.

BACKGROUND

Prostate Cancer is the most prevalent cancer among men in the United Stated and is their second leading cause of death. Prostatectomy and radiotherapy have been the mainstay treatment for men with localized prostate cancer. However, wide variations in the incidence of positive surgical margins (11%-48%) have been reported at the time of radical prostatectomy and have been repeatedly demonstrated to be associated with greater rates of biochemical and local recurrence. Achieving a negative surgical margin may be an opportunity for the surgeon to improve surgical impact on the disease.

Surgeons predominately use visual examination and palpation during surgery to determine the extent of the tissues to be removed; however, these are insufficient to confirm all tumor sites, particularly for some nonpalpable and invisible occult tumors. Adjuvant radiotherapy and chemotherapy often result in failure to halt disease and are associated with severe side effects, and there is an urgent need for better approaches. To fill this need, fluorescence image-guided surgery (IGS) has been developed which, compared with white light surgery (WLS), can identify cancerous tissue, delineate tumor margins, and potentially reduce damage to important normal structures.

Photodynamic therapy, hereinafter also referred to as "PDT", is a process for treating cancer wherein visible light is used to activate a substance, such as a dye or drug, which then attacks the tumor tissue through one or more photochemical reactions, thereby producing a cell-killing, or cytotoxic, effect. When certain photosensitizer compounds are applied to a human or animal body, they are selectively retained by cancerous tissue while being eliminated by healthy tissue. The tumor or cancerous tissue containing the photosensitizer can then be exposed to therapeutic light of an appropriate wavelength and at a specific intensity for activation. The light energy and the photosensitizer cause a photochemical reaction that kills the cells in which the photosensitizer resides.

Phthalocyanines, hereinafter also abbreviated as "Pcs", are a group of photosensitizer compounds having the phthalocyanine ring system. Phthalocyanines are azaporphyrins consisting of four benzoindole groups connected by nitrogen bridges in a 16-membered ring of alternating carbon and nitrogen atoms (i.e., $C_{32}H_{16}N_8$) which form stable chelates with metal and metalloid cations. In these compounds, the ring center is occupied by a metal ion (either a diamagnetic or a paramagnetic ion) that may, depending on the ion, carry one or two ligands. In addition, the ring periphery may be either unsubstituted or substituted. The synthesis and use of a wide variety of phthalocyanines in photodynamic therapy is described in International Publication WO 2005/099689. Phthalocyanines strongly absorb clinically useful red or near IR radiation with absorption peaks falling between about 600 and 810 nm, which potentially allows deep tissue penetration by the light.

SUMMARY

Embodiments described herein relate to the use of pharmaceutical compositions including PSMA-targeted phthalocyanine compounds for use in the treatment of PSMA expressing cancers and particularly for use in methods of treating PSMA expressing cancers combining image guided surgery (IGS) and photodynamic therapy (PDT). The phthalocyanine compounds coupled to a PSMA moiety described herein are based on analogs of the PDT photosensitizing compound Pc4. These analogs have been found to be effective in targeted bioimaging of PSMA expressing cancer cells, intraoperative guided surgery and/or targeted PDT of cancer in a subject.

Some embodiments described herein relate to a method of treating a PSMA expressing cancer. The method includes administering to a subject with a PSMA expressing cancer a therapeutically effective amount of a pharmaceutical composition. The pharmaceutical composition includes a PSMA-targeted phthalocyanine compound having the formula (I):

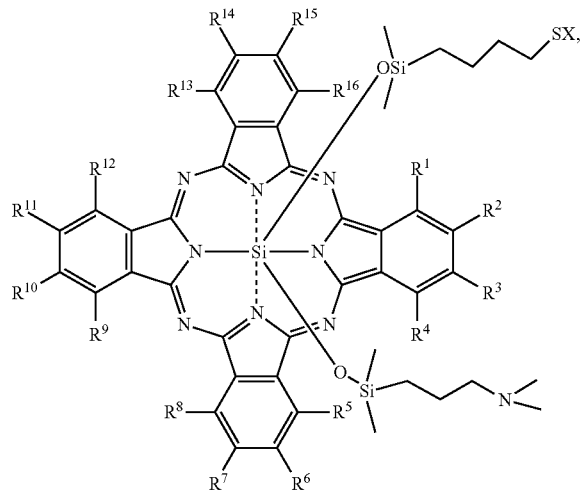

wherein X is a PSMA targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

The method also includes detecting the PSMA-targeted phthalocyanine compound bound to and/or complexed with the cancer cells to determine the location and/or distribution of the cancer cells in the subject, surgically resecting the cancer in the subject, wherein the detected PSMA-targeted phthalocyanine compound bound to and/or complexed with the cancer cells guide surgical resection of the cancer, and irradiating the PSMA-targeted phthalocyanine compound in the site of surgical resection, thereby inducing the cytotoxic effects of the phthalocyanine compound on residual cancer cells following surgical resection.

In some embodiments, the PSMA ligand can include a PSMA-1 ligand. In some embodiments, intra-operative imaging (IOI) of the PSMA-targeted phthalocyanine compound bound to and/or complexed with the cancer cells defines a tumor margin in the subject to guide surgical resection of the cancer. In some embodiments, the surgical resection site is irradiated with an amount of radiation effective to inhibit tumor recurrence in the subject.

In some embodiments, $R^1$-$R^{16}$ are independently selected from the group consisting of hydrogen, halogen, nitro, cyano, hydroxyl, thiol, amino, and methyl.

In other embodiments, the PSMA-targeted phthalocyanine compound can have the formula (II):

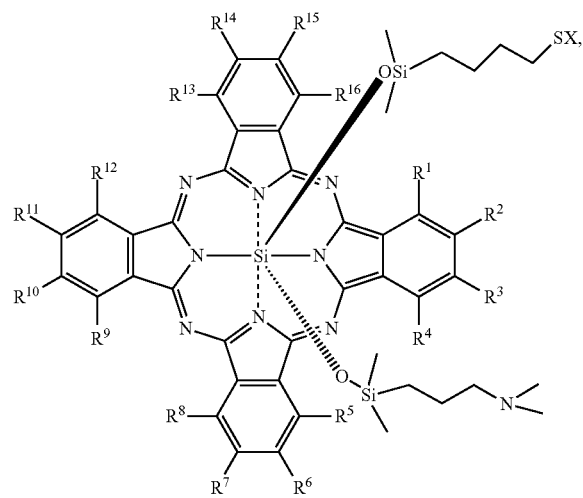

wherein X is a PSMA targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In still other embodiments, the PSMA-targeted phthalocyanine compound can have the formula (III):

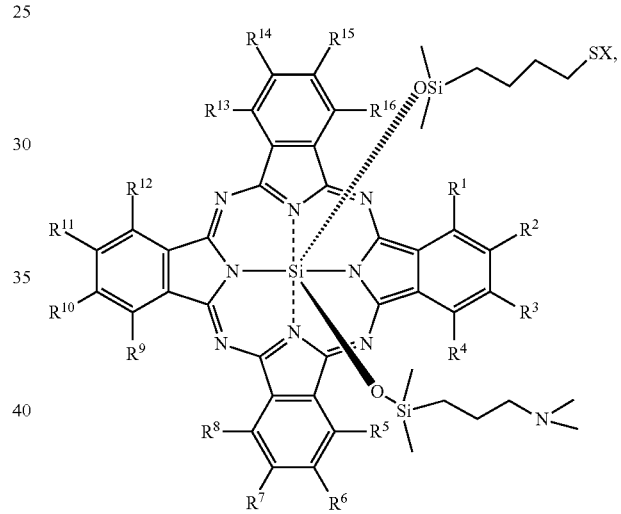

wherein X is a PSMA targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In certain embodiments, the PSMA-targeted phthalocyanine compound has the formula (IV):

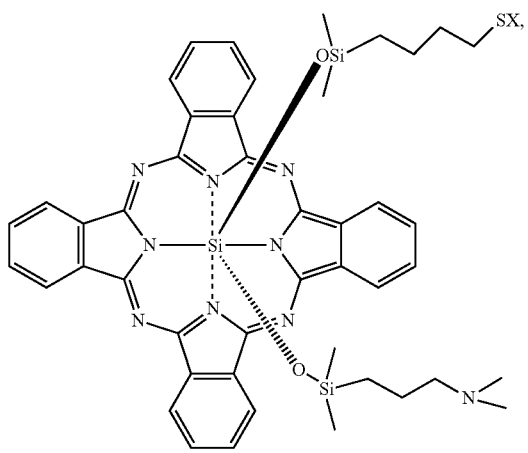

wherein X is a PSMA-1 ligand; and pharmaceutically acceptable salts thereof.

In some embodiments, the PSMA targeted phthalocyanine compound is administered by intravenous injection. In some embodiments, the PSMA targeted phthalocyanine compound is formulated in a pharmaceutically acceptable carrier.

In some embodiments, the PSMA expressing cancer is selected from the group consisting of renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. In some embodiments, the cancer is metastatic prostate cancer.

Other embodiments described herein relate to a method of treating prostate cancer in a subject. The method includes administering to a subject with prostate cancer a therapeutically effective amount of a pharmaceutical composition. The pharmaceutical composition includes a PSMA-targeted phthalocyanine compound having the formula (I):

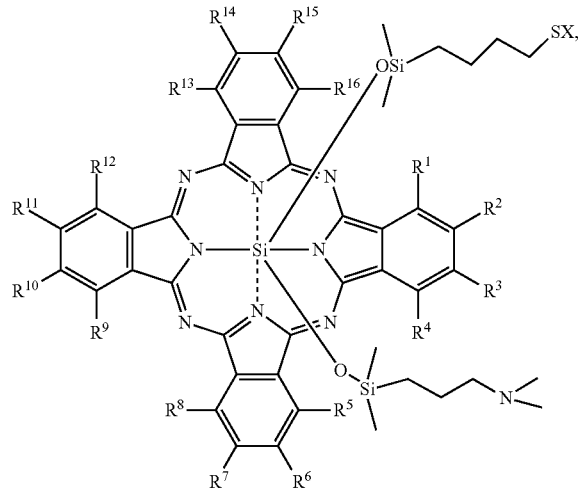

wherein X is a PSMA targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

The method also includes detecting the PSMA-targeted phthalocyanine compound bound to and/or complexed with the prostate cancer cells to determine the location and/or distribution of the prostate cancer cells in the subject, surgically resecting the prostate cancer in the subject, wherein the detected PSMA-targeted phthalocyanine compound bound to and/or complexed with the prostate cancer cells guide surgical resection of the cancer, and irradiating the PSMA-targeted phthalocyanine compound in the site of surgical resection, thereby inducing the cytotoxic effects of the phthalocyanine compound on residual prostate cancer cells following surgical resection.

In some embodiments, the PSMA ligand can include a PSMA-1 ligand. In some embodiments, intra-operative imaging (IOI) of the PSMA-targeted phthalocyanine compound bound to and/or complexed with the prostate cancer cells defines a tumor margin in the subject to guide surgical resection of the cancer. In some embodiments, the surgical resection site is irradiated with an amount of radiation effective to inhibit tumor recurrence in the subject.

In some embodiments, $R^1$-$R^{16}$ are independently selected from the group consisting of hydrogen, halogen, nitro, cyano, hydroxyl, thiol, amino, and methyl.

In other embodiments, the PSMA-targeted phthalocyanine compound can have the formula (II):

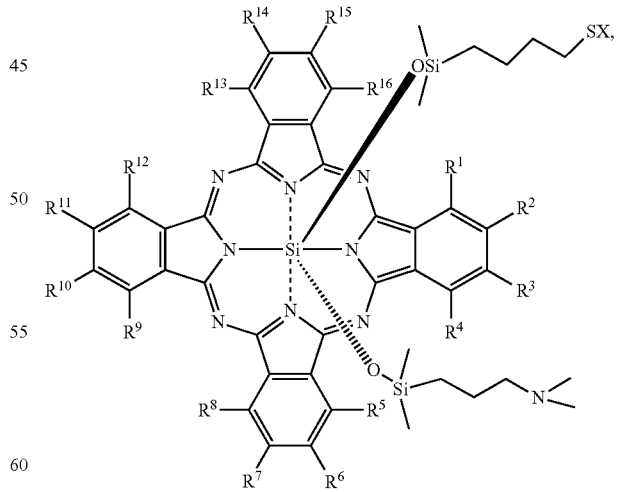

wherein X is a PSMA targeting moiety;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In still other embodiments, the PSMA-targeted phthalocyanine compound can have the formula (III):

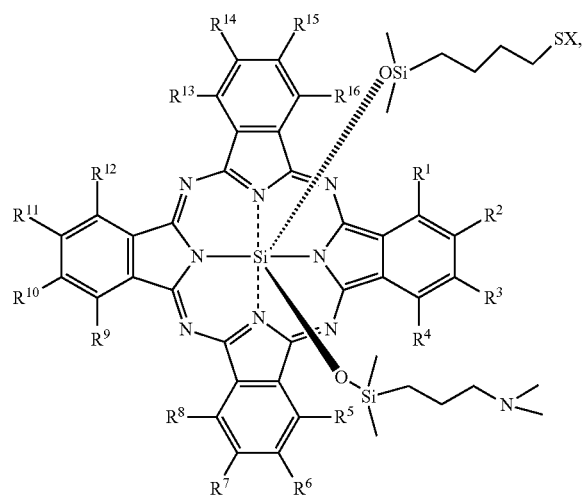

wherein X is a PSMA targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In some embodiments, $R^1$-$R^{16}$ are independently selected from the group consisting of hydrogen, halogen, nitro, cyano, hydroxyl, thiol, amino, and methyl.

In certain embodiments, the PSMA-targeted phthalocyanine compound has the formula (IV):

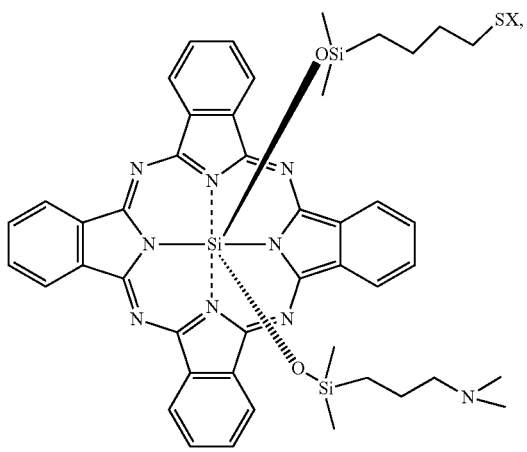

wherein X is a PSMA-1 ligand; and pharmaceutically acceptable salts thereof.

In some embodiments, the PSMA targeted phthalocyanine compound is administered by intravenous injection. In some embodiments, the PSMA targeted phthalocyanine compound is formulated in a pharmaceutically acceptable carrier.

BRIEF DESCRIPTION OF THE DRAWINGS

The following is a brief description of the drawings which are presented for the purpose of illustrating the invention and not for the purpose of limiting them.

DETAILED DESCRIPTION

Figure 1A:
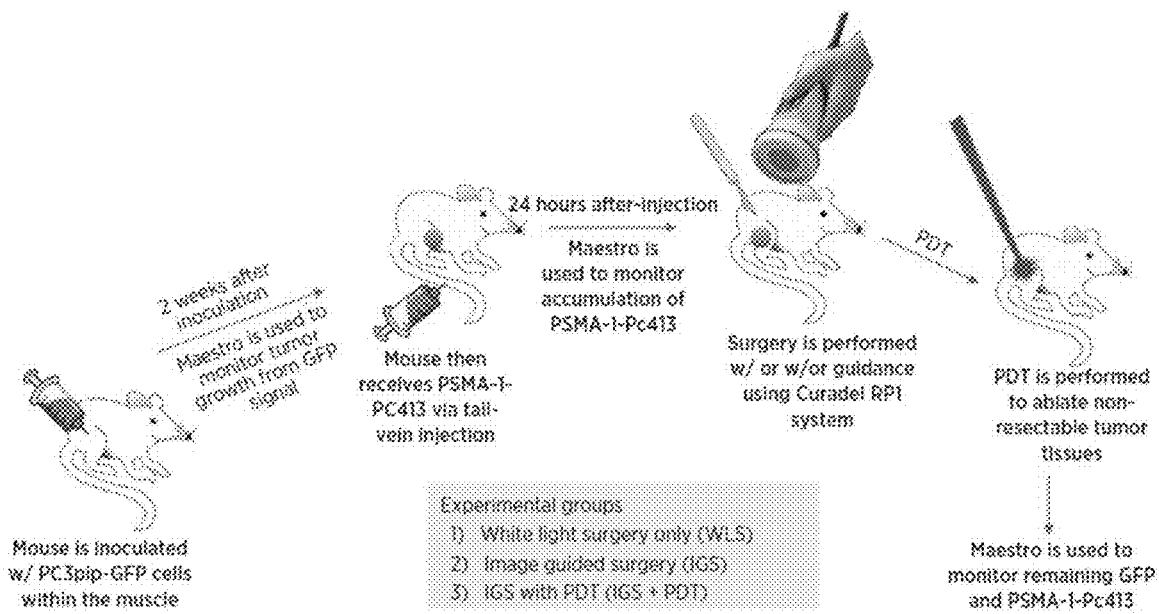
FIGS. 1(A-B) illustrate the experimental design and generation of ROS in vivo. (A) Scheme of experimental design. (B) Detection of ROS in vivo after PDT. Mice bearing PC3pip tumor received PSMA-1-Pc413 and 24 hours later were administered ROSstar800cw, which detects ROS. Both PSMA-1-Pc413 and ROSstar800cw fluorescence were measured before and after light irradiation. Fluorescent signal in the deep red channel was observed after PDT, indicating generation of ROS after PDT.

All scientific and technical terms used in this application have meanings commonly used in the art unless otherwise specified. The definitions provided herein are to facilitate understanding of certain terms used frequently herein and are not meant to limit the scope of the application.

The term "alkoxy" refers to an alkyl group having an oxygen attached thereto. Representative alkoxy groups include methoxy, ethoxy, propoxy, tert-butoxy and the like. An "ether" is two hydrocarbon groups covalently linked by an oxygen. Accordingly, the substituent of an alkyl that renders that alkyl an ether is or resembles an alkoxy.

The terms "amine" and "amino" are art-recognized and refer to both unsubstituted and substituted amines and salts thereof.

The term "aryl" as used herein includes 5-, 6-, and 7-membered substituted or unsubstituted single-ring aromatic groups in which each atom of the ring is carbon. Aryl groups include benzene, phenol, aniline, and the like.

The terms "carbocycle" and "carbocyclyl", as used herein, refer to a non-aromatic substituted or unsubstituted ring in which each atom of the ring is carbon.

The terms "heteroaryl" includes substituted or unsubstituted aromatic 5- to 7-membered ring structures, more preferably 5- to 6-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms.

The term "substituted" refers to moieties having substituents replacing a hydrogen on one or more carbons of the framework. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

Substituents on fused ring structures can be peripheral or non-peripheral substituents. A non-peripheral substituent, as defined herein, is a substituent which is adjacent (i.e., a) to the point of fusion between an outer phenyl ring and an inner pyrrole ring, as found in phthalocyanine compounds as exemplified by Formula (I) herein. A substituent is peripheral, on the other hand, when it is not a non-peripheral substituent. For example, in Formula I provided herein, the substituents $R^2$, $R^3$, $R^6$, $R^7$, $R^{10}$, $R^{11}$, $R^{14}$, and R are peripheral substituents.

As used herein, the term "targeting moiety" can refer to a molecule or molecules that are able to bind to and complex with a biomarker. The term can also refer to a functional group that serves to target or direct a compound described herein to a particular location, cell type, diseased tissue, or association. In general, a "targeting moiety" can be directed against a biomarker.

As used herein, the term "molecular signature" can refer to a unique expression pattern of one or more biomarkers (e.g., gene(s) or protein(s)) of a cell.

As used herein, the term "neoplastic disorder" can refer to a disease state in a subject in which there are cells and/or tissues which proliferate abnormally. Neoplastic disorders can include, but are not limited to, cancers, sarcomas, tumors, leukemias, lymphomas, and the like.

As used herein, the term "neoplastic cell" can refer to a cell that shows aberrant cell growth, such as increased, uncontrolled cell growth. A neoplastic cell can be a hyperplastic cell, a cell from a cell line that shows a lack of contact inhibition when grown in vitro, a tumor cell, or a cancer cell that is capable of metastasis in vivo. Alternatively, a neoplastic cell can be termed a "cancer cell." Non-limiting examples of cancer cells can include melanoma, breast cancer, ovarian cancer, prostate cancer, sarcoma, leukemic retinoblastoma, hepatoma, myeloma, glioma, mesothelioma, carcinoma, leukemia, lymphoma, Hodgkin lymphoma, Non-Hodgkin lymphoma, promyelocytic leukemia, lymphoblastoma, thymoma, lymphoma cells, melanoma cells, sarcoma cells, leukemia cells, retinoblastoma cells, hepatoma cells, myeloma cells, glioma cells, mesothelioma cells, and carcinoma cells.

As used herein, the term "tumor" can refer to an abnormal mass or population of cells that result from excessive cell division, whether malignant or benign, and all pre-cancerous and cancerous cells and tissues.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition. As used herein, the terms "treating" or "treatment" of a cancer can refer to executing a treatment protocol to eradicate at least one cancer cell. Thus, "treating" or "treatment" does not require complete eradication of cancer cells.

"PSMA" refers to Prostate Specific Membrane Antigen, a potential carcinoma marker that has been hypothesized to serve as a target for imaging and cytotoxic treatment modalities for cancer.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, aves, etc.), which is to be the recipient of a particular treatment.

Embodiments described herein relate to the use of prostate specific membrane antigen (PSMA)-targeted phthalocyanine compounds for use in the treatment of PSMA expressing cancers and particularly for use in PSMA expressing cancer treatment methods combining image-guided surgery (IGS) and photodynamic therapy (PDT).

It was found that a PSMA-targeted phthalocyanine compound photodynamic agent was able to improve the visualization of tumor margins, enhance surgical cancer resection during image-guided surgery compared to white light surgical resection, and effectively destroy undetectable and/or unresectable localized cancers using post-surgical PDT. We have shown that a PSMA-targeted phthalocyanine compound used as a PDT agent alone, i.e., without prior surgery, is sufficient to eradicate primary tumors in a subject but in 100% of the cases, the tumors recurred. While the tumor burden is too large for PDT alone to effectively eradicate all tumor cells, it was shown that therapeutic methods including surgical resection using a PSMA-targeted phthalocyanine compound prior to PDT reduces the tumor burden, thereby allowing for more effective eradication of cancer cells and significantly reduced tumor recurrence and improved survival of the subject.

Methods of treating a PSMA expressing cancer include administering to a subject with a PSMA expressing cancer a therapeutically effective amount of a pharmaceutical composition, the pharmaceutical composition including a PSMA-targeted phthalocyanine compound. The PSMA-targeted phthalocyanine compound conjugates described herein are based on analogs of the PDT photosensitizing compound Pc4 and have been found to be effective in targeted bioimaging of PSMA expressing cancer cells, intraoperative guided surgery (IGS) and/or targeted PDT of cancer in a subject.

In some embodiments, a pharmaceutical composition administered to a subject can include a PSMA-targeted phthalocyanine compound having the formula (I):

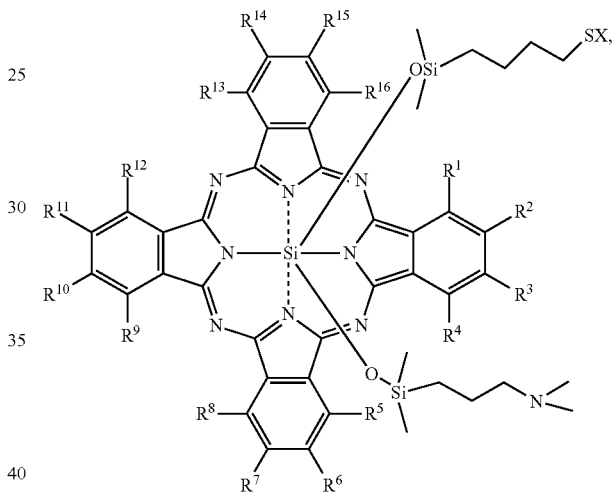

wherein X is a PSMA targeting moiety;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

In certain embodiments, $R^1$-$R^{16}$ of the compound of formula (I) are independently selected from the group consisting of hydrogen, halogen, nitro, cyano, hydroxyl, thiol, amino, and methyl, while in other embodiments $R^1$-$R^{16}$ are all hydrogen.

In other embodiments, the PSMA-targeted phthalocyanine compound can have the formula (II):

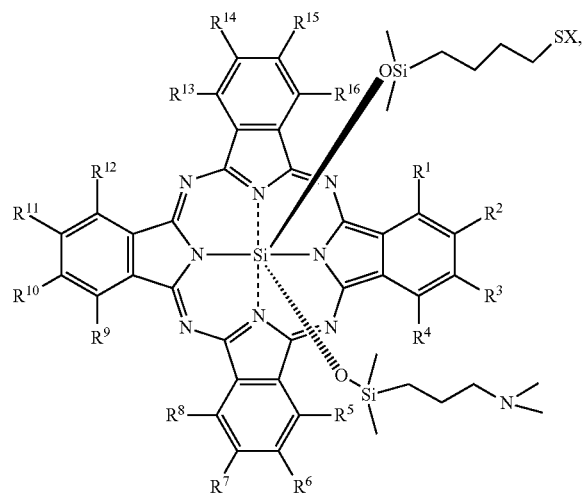

wherein X is a PSMA targeting moiety;

R$^1$, R$^4$, R$^5$, R$^8$, R$^9$, R$^{12}$, R$^{13}$, and R$^{16}$ are each independently selected from the group consisting of hydrogen, halogen, nitro, cyano, hydroxyl, thiol, amino, and methyl;

R$^2$, R$^3$, R$^6$, R$^7$, R$^{10}$, R$^{11}$, R$^{14}$, and R$^{15}$ are each independently selected from the group consisting of hydrogen, halogen, nitro, cyano, hydroxyl, thiol, amino, carboxy, aryl, heteroaryl, carbocyclyl, heterocyclyl, C$_{1-6}$ alkyl, C$_{1-6}$ alkenyl, C$_{1-6}$ alkynyl, C$_{1-6}$ alkoxy, C$_{1-6}$ acyl, C$_{1-6}$ alkylcarbonyloxy, C$_{1-6}$ carbocyclylalkyl, C$_{1-6}$ aminoalkyl, C$_{1-6}$ alkylamino, C$_{1-6}$ thioalkyl, C$_{1-6}$ alkylthio, C$_{1-6}$ hydroxyalkyl, C$_{1-6}$ alkyloxycarbonyl, C$_{1-6}$ alkylaminocarbonyl, and C$_{1-6}$ alkylcarbonylamino; and pharmaceutically acceptable salts thereof.

In some embodiments, R$^1$-R$^{16}$ are independently selected from the group consisting of hydrogen, halogen, nitro, cyano, hydroxyl, thiol, amino, and methyl.

In still other embodiments the PSMA-targeted phthalocyanine compound can have the formula (III):

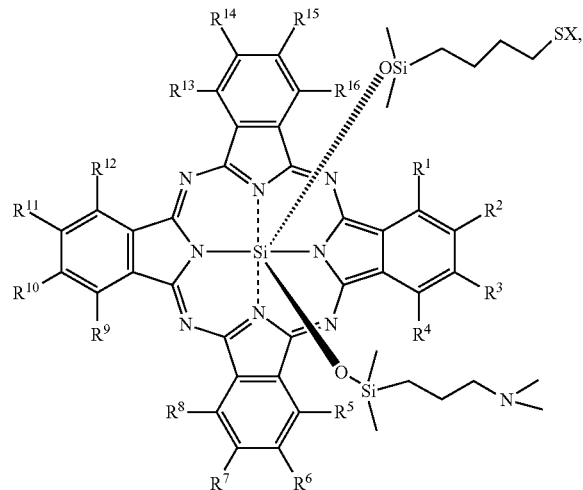

wherein X is a PSMA targeting moiety;

R$^1$, R$^4$, R$^5$, R$^8$, R$^9$, R$^{12}$, R$^{13}$, and R$^{16}$ are each independently selected from the group consisting of hydrogen, halogen, nitro, cyano, hydroxyl, thiol, amino, and methyl;

R$^2$, R$^3$, R$^6$, R$^7$, R$^{10}$, R$^{11}$, R$^{14}$, and R$^{15}$ are each independently selected from the group consisting of hydrogen, halogen, nitro, cyano, hydroxyl, thiol, amino, carboxy, aryl, heteroaryl, carbocyclyl, heterocyclyl, C$_{1-6}$ alkyl, C$_{1-6}$ alkenyl, C$_{1-6}$ alkynyl, C$_{1-6}$ alkoxy, C$_{1-6}$ acyl, C$_{1-6}$ alkylcarbonyloxy, C$_{1-6}$ carbocyclylalkyl, C$_{1-6}$ aminoalkyl, C$_{1-6}$ alkylamino, C$_{1-6}$ thioalkyl, C$_{1-6}$ alkylthio, C$_{1-6}$ hydroxyalkyl, C$_{1-6}$ alkyloxycarbonyl, C$_{1-6}$ alkylaminocarbonyl, and C$_{1-6}$ alkylcarbonylamino; and pharmaceutically acceptable salts thereof.

In some embodiments, R$^1$-R$^{16}$ are independently selected from the group consisting of hydrogen, halogen, nitro, cyano, hydroxyl, thiol, amino, and methyl.

In certain embodiments, the PSMA targeted phthalocyanine compound of formula (I) can have the formula: the PSMA-targeted phthalocyanine compound has the formula (IV):

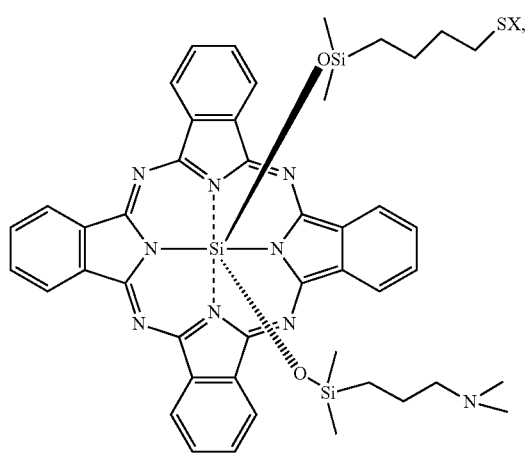

wherein X is a PSMA ligand; or a pharmaceutically acceptable salt thereof.

In some embodiments, the phthalocyanine compound can be indirectly or directly coupled or conjugated to at least one PSMA-targeting moiety to target and/or adhere the phthalocyanine compound to a PSMA expressing cell or tissue of interest. The targeted conjugate including the phthalocyanine compound and the PSMA-targeting moiety are administered to a subject for a combination of diagnostic, therapeutic, and/or theranostic applications in accordance with the methods described herein.

Without being bound by theory, it is believed that the PSMA-targeted phthalocyanine compound of formula (I) can exploit the expression of the distinct biochemical marker, PSMA, found for example on the surface of most prostate cancer cells, thus significantly reducing both off-target effects and toxicity. The PSMA targeting moiety can include any molecule, or complex of molecules, which is/are capable of interacting with the cell surface PSMA glycoprotein biomarker of a PSMA expressing cancer cell. The PSMA-targeting moiety can interact with the PSMA glycoprotein cell surface biomarker through non-covalent binding, covalent binding, hydrogen binding, van der Waals forces, ionic bonds, hydrophobic interactions, electrostatic interaction, and/or combinations thereof.

The PSMA-targeting moiety can be directly or indirectly coupled or conjugated to the axial thiol group or terminating ligand attached to the central silicon metalloid of the phthalocyanine compound of formula (I). In exemplary embodiments, the PSMA-targeting moiety is directly coupled or conjugated to the axial thiol group or terminating ligand attached to the central silicon metalloid of the phthalocyanine compound of formula (I). In other embodiments, the phthalocyanine compound can be indirectly coupled or conjugated to the targeting moiety via a linker. The linker can be of any suitable length and contain any suitable number of atoms and/or subunits. The linker can include one or a combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof. In exemplary embodiments, the phthalocyanine compound can be indirectly coupled or conjugated to the PSMA-targeting moiety via a sulfosuccinimidyl-4-(N-maleimidomethyl)cyclohexane-1-carboxylate (sulfo-SMCC) linker.

The PSMA targeting moiety can include, but is not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the PSMA targeting moiety can include an antibody, such as a monoclonal antibody, a polyclonal antibody, or a humanized antibody, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent targeting moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

Preparation of antibodies may be accomplished by any number of well-known methods for generating antibodies. These methods typically include the step of immunization of animals, typically mice, with a desired immunogen (e.g., a desired target molecule or fragment thereof). Once the mice have been immunized and boosted one or more times with the desired immunogen(s), antibody-producing hybridomas may be prepared and screened according to well-known methods. See, for example, Kuby, Janis, Immunology, Third Edition, pp. 131-139, W.H. Freeman & Co. (1997), for a general overview of monoclonal antibody production, that portion of which is incorporated herein by reference.

The PSMA-targeting moiety need not originate from a biological source. The PSMA targeting moiety may, for example, be screened from a combinatorial library of synthetic peptides. One such method is described in U.S. Pat. No. 5,948,635, incorporated herein by reference, which describes the production of phagemid libraries having random amino acid insertions in the pIII gene of M13. These phage may be clonally amplified by affinity selection.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting moiety and select for a targeting moiety with superior binding characteristics as compared to the un-mutated targeting moiety. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the PSMA targeting moiety may be modified to make them more resistant to cleavage by proteases. For example, the stability of a PSMA targeting moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting moiety may be of the D configuration. The switch from L to D amino acids neutralizes the digestion capabilities of many of the ubiquitous peptidases found in the digestive tract. Alternatively, enhanced stability of a PSMA targeting moiety comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a PSMA-targeting moiety may be achieved by intercalating one or more dextrorotatory amino acids (such as, dextrorotatory phenylalanine or dextrorotatory tryptophan) between the amino acids of targeting moiety. In some embodiments, such modifications increase the protease resistance of a PSMA-targeting moiety without affecting the activity or specificity of the interaction with a desired target molecule.

In certain embodiments, the antibodies or variants thereof may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature, 321, 522-525 or Tempest et al. (1991), Biotechnology, 9, 266-273. In addition, transgenic mice, or other mammals, may be used to express humanized antibodies. Such humanization may be partial or complete.

In certain embodiments, a PSMA-targeting moiety as described herein may comprise a homing peptide, which selectively directs the pthalocyanine compound to a targeted PSMA expressing cell. Homing peptides for a targeted cell can be identified using various methods well known in the art.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol. 124:373-380), and to the human urokinase receptor (Goodson, et al., 1994, Proc. Natl. Acad. Sci., USA 91:7129-7133).

In certain embodiments, the PSMA-targeting moiety may comprise a receptor molecule, including, for example, receptors, which naturally recognize PSMA on the cell surface of a target cell. Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In still other embodiments, the PSMA-targeting moiety may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the PSMA-targeting moiety may be a peptidomimetic. By employing, for example, scanning mutagenesis to map the amino acid residues of a protein, which is involved in binding other proteins, peptidomimetic compounds can be generated that mimic those residues, which facilitate the interaction. Such mimetics may then be used as a PSMA targeting moiety to deliver the phthalocyanine compound to a target PSMA expressing cancer cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

In certain embodiments, the PSMA-targeting moiety may comprise a ligand molecule, including, for example, ligands that naturally recognize the PSMA receptor of a PSMA expressing target cancer cell. Such ligand molecules include ligands that have been modified to increase their specificity of interaction with a target receptor, ligands that have been modified to interact with a desired receptor not naturally recognized by the ligand, and fragments of such ligands.

By way of example, the PSMA-targeting moiety can comprise a PSMA ligand. PSMA is highly expressed in prostate cancer expression. Pathological studies indicate that PSMA is expressed by virtually all prostate cancers, and its expression is further increased in poorly differentiated, metastatic, and hormone-refractory carcinomas. Higher PSMA expression is also found in cancer cells from castration-resistant prostate cancer patients. Increased PSMA expression is reported to correlate with the risk of early prostate cancer recurrence after radical prostatectomy. In addition to being overexpressed in prostate cancer (PCa), PSMA is also expressed in the neovasculature of neoplasms including but not limited to conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the PSMA ligand has the general formula (V):

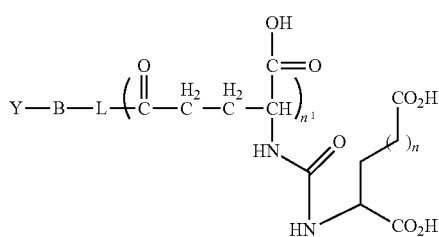

wherein:
n and $n^1$ are each independently 1, 2, 3, or 4;
L is an optionally substituted aliphatic or heteroaliphatic linking group;
B comprises at least one negatively charged amino acid; and
Y is a phthalocyanine compound of formula (I) that is directly or indirectly linked or coupled to B.

In other embodiments, L can be an optionally substituted aliphatic or heteroaliphatic group that includes at least one ring selected from the group consisting of an optionally substituted 4 to 7 membered nonaromatic heterocyclic ring and an optionally substituted C4-C7 cycloalkyl ring.

An aliphatic group is a straight chained, branched or cyclic non-aromatic hydrocarbon, which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group (preferably C1-C4 straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

Suitable optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C(H$_2$)—) can form one or two single bonds to one or two substituents (e.g., —C(alkyl)(Br))—, —C(alkyl)(H)—) or a double bond to one substituent (e.g., —C=O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —POR$^a$R$^b$, PO$_2$R$^a$R$^b$, —PO$_3$R$^a$R$^b$, —PO$_4$R$^a$R$^b$, —P(S)R$^a$R$^b$, —P(S)OR$^a$R$^b$, —P(S)O$_2$R$^a$R$^b$, —P(S)O$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CRC=CR$^a$R$^b$, —C=CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$—R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group. Also contemplated are isomers of these groups.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counter anions are provided in the section below directed to suitable pharmacologically acceptable salts.

In other embodiments, B can include at least one, two, three, four, or more negatively charged amino acids, i.e., amino acids with a negative charged side chain, such as glutamic acid, aspartic acid, and/or tyrosine. B can also include other amino acids that facilitate binding of B to Y and/or the PSMA ligand to a detectable moiety, therapeutic agent, and/or theranostic agent.

In some embodiments, B can have the following formula:

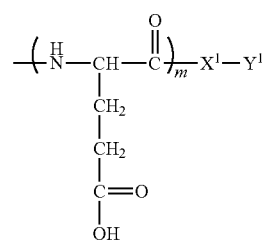

wherein m is 1, 2, 3, or 4, $X^1$ is an amino acid, and $Y^1$ is a phthalocyanine compound of formula (I) that is directly or indirectly linked to $X^1$.

In other embodiments, B can have the following formula:

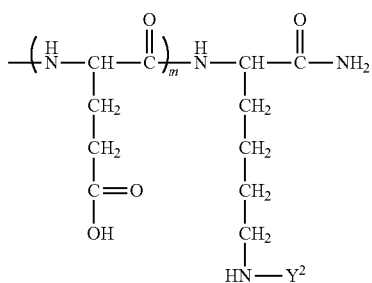

wherein m is 1, 2, 3, or 4 and $Y^2$ is a phthalocyanine compound of formula (I) that is directly or indirectly linked to B. In other embodiments, the PSMA ligand can have the general formula:

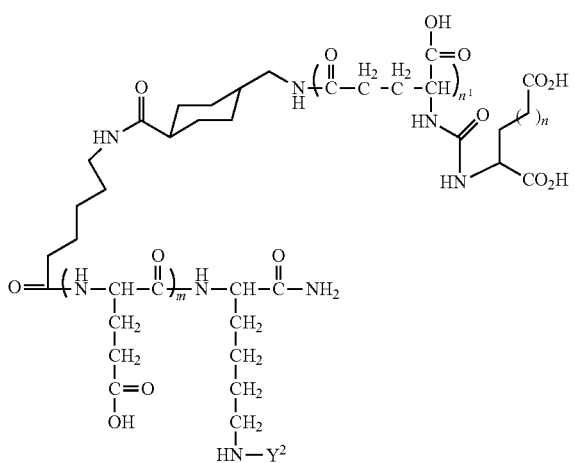

wherein m, n, and $n^1$ are independently 1, 2, 3, or 4; and $Y^2$ is a phthalocyanine compound of formula (I) that is directly or indirectly linked to the PSMA ligand.

In exemplary embodiments, the PSMA-targeting moiety can comprise a highly negatively charged PSMA ligand (e.g., PSMA-1). In accordance with a method described herein, PSMA-targeted phthalocyanine compound can provide image guidance for prostate tumor resection and allow subsequent targeted PDT to eliminate unresectable or remaining cancer cells.

The PSMA-targeted phthalocyanine compound provided in a pharmaceutical composition can be formulated in a pharmaceutically acceptable carrier. "Pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In some embodiments, aqueous-based or oil-based pharmaceutically acceptable carriers can be used. An aqueous-based pharmaceutically acceptable carrier is a polar solution primarily consisting of water, and including solutions such as pyrogen-free water, isotonic saline, Ringer's solution, and phosphate buffer solutions. Oil-based pharmaceutically acceptable carriers, on the other hand, are relatively non-polar solutions consisting primarily of oils or other relatively non-polar organic solvents. Examples of oil-based pharmaceutically acceptable carriers include various organic solvents, mineral oil, vegetable oil, and petrolatum.

In some embodiments, pharmaceutical compositions including the PSMA-targeted phthalocyanine compounds can be formulated for systemic or topical administration. Systemic administration includes delivery of an aqueous solution, preferably a buffered aqueous solution, including a phthalocyanine compound or targeted conjugate thereof. Systemic formulations typically also include a dispersant. Systemic administration is typically done parenterally (e.g., intravenously or intramuscularly). However, systemic administration can also be carried out by oral administration. By way of example, pharmaceutical compositions including PSMA-targeted phthalocyanine compounds described herein can be intravenously administered to a subject that is known to or suspected of having a PSMA expressing tumor.

Topical administration of PSMA-targeted phthalocyanine compounds can be accomplished using various different formulations such as powders, sprays, ointments, pastes, creams, lotions, gels, solutions, or patches. The active component may be mixed under sterile conditions with a pharmaceutically acceptable carrier, and with any preservatives, buffers, or propellants which may be required. The ointments, pastes, creams, solutions, foams, lacquers, oils and gels may contain excipients in addition to phthalocyanine(s). These formulations may contain a phthalocyanine salt within or on micro or nanoparticles, liposomes, beads, polymer matrices, sponges, osmotic pumps, or other structures.

PSMA-targeted phthalocyanine compounds can be formulated as ointments or creams for topical administration. Ointments are homogeneous, semi-solid preparations intended for external application to the skin or mucous membranes. They are used as emollients or for the application of active ingredients to the skin for protective, therapeutic, or prophylactic purposes and where a degree of occlusion is desired. Ointments can be formulated using hydrophobic, hydrophilic, or water-emulsifying bases to provide preparations for various applications. Creams, on the other hand, are semi-solid emulsions; i.e., a mixture of oil and water. They are divided into two types: oil-in-water creams that are composed of small droplets of oil dispersed in a continuous aqueous phase, and water-in-oil creams that are composed of small droplets of water dispersed in a continuous oily phase.

PSMA-targeted phthalocyanine compounds can also be administered by aerosol. This is accomplished by preparing an aqueous aerosol, liposomal preparation, or solid particles containing the compound. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers.

PSMA-targeted phthalocyanine compounds can also be formulated for delivery as a gel. Gel formulations comprising a PSMA-targeted phthalocyanine compound or salt thereof may be prepared according to U.S. Pat. No. 6,617,356 or 5,914,334, the disclosures of which are incorporated herein in their entirety. In addition, PSMA-targeted phthalocyanine compound-containing gels can be dried to form films suitable for phthalocyanine administration.

Transdermal patches have the added advantage of providing controlled delivery of a phthalocyanine to the body. Such dosage forms can be made by dissolving or dispersing the agent in the proper medium. Absorption enhancers can also be used to increase the flux of the photosensitizer(s) into the skin. The rate of such flux can be controlled by either providing a rate controlling membrane or dispersing the agent in a polymer matrix or gel.

Pharmaceutical compositions including PSMA-targeted phthalocyanine compounds can also be delivered transdermally using microneedles. See for example Arora et al., International Journal of Pharmaceutics, 364, pg. 227-236 (2008), which describes micro-scale devices for transdermal drug delivery.

Delivery of pharmaceutical compositions including PSMA-targeted phthalocyanine compounds described herein across an epithelial, epidermal, serosal or mucosal surface may be accomplished using application of an electrical current and a charged solvent solution, such as iontophoresis.

PSMA-targeted phthalocyanine compound compositions can be formulated to allow delivery in sufficient amounts and for a period of time(s) to be detectable, imaging effective and therapeutically effective. Single or multiple administrations of the probe can be given.

A PSMA-targeted phthalocyanine compound composition described herein can be administered to a subject in a detectable and/or imaging effective quantity. A "detectable quantity" means that the amount of the detectable compound that is administered is sufficient to enable detection of binding of the PSMA-targeted phthalocyanine compound to the PSMA expressing cancer cell. An "imaging effective quantity" means that the amount of the detectable compound that is administered is sufficient to enable imaging of binding of the compound to the targeted PSMA expressing cancer cells. For example, the imaging effective quantity can be the amount sufficient to enable detection PSMA-targeted phthalocyanine compound bound to the PSMA expressing cancer followed by intraoperative imaging during image guided surgical resection of cancer in a subject. In certain embodiments, the therapeutically effective amount is the amount sufficient to enable the induction of cytotoxic effects of the PSMA-targeted phthalocyanine compound using PDT on residual cancer cells following detection and surgical resection of the cancer. In exemplary embodiments, a PSMA-targeted phthalocyanine compound composition is administered at a dose of about 0.5 mg/kg to a subject for use in the detection of binding of the PSMA-targeted phthalocyanine compound to the PSMA expressing cancer cells, image guided surgical resection of the detected cancer cells, and subsequent PDT treatment on residual cancer cells following surgical resection in accordance with a method described herein.

Once administered to a subject, a pharmaceutical composition including PSMA-targeted phthalocyanine compound bound to and/or complexed with the PSMA expressing cancer cells is detected to determine the presence, location, and/or distribution of PSMA expressing cancer cells or PSMA expressing neovaculature of the cancer cells in an organ or body area of a subject. The presence, location, and/or distribution of the PSMA-targeting moiety coupled to a detectable phthalocyanine compound in the animal's tissue, e.g., prostate tissue, can be visualized (e.g., with an in vivo imaging modality). In an exemplary embodiment, the presence, location, and/or distribution of the PSMA-targeted phthalocyanine compound bound to and/or complexed with the PSMA expressing cancer cells can be visualized about 24 hours after the pharmaceutical composition is administered to the subject.

The imaging modality can include one or a combination of known imaging techniques capable of visualizing the PSMA-targeted phthalocyanine compound. Examples of imaging modalities can include ultrasound (US), magnetic resonance imaging (MRI), nuclear magnetic resonance (NMR), computed topography (CT), electron spin resonance (ESR), nuclear medical imaging, optical imaging, and positron emission topography (PET). The imaging modality can then be operated to generate a visible image of the presence, location, and/or distribution of PSMA expressing cancer cells.

"Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the PSMA-targeting moiety coupled to a detectable phthalocyanine compound may then be correlated with the presence or absence of PSMA expressing cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject. In one embodiment, pharmaceutical compositions including a PSMA-targeted phthalocyanine compound are administered to a subject to assess the distribution of targeted cancerous tumor cells in a subject and correlate the distribution to a specific location.

Following detection of PSMA-targeted phthalocyanine compounds bound to and/or complexed with the PSMA expressing cancer cells, the detected cancer is used to define a tumor margin and guide surgical resection of the cancer from the subject. Surgeons routinely use stereotactic techniques and intra-operative MRI (iMRI) in surgical resections. This allows them to specifically identify and resect tissue from distinct regions of the tumor such as the tumor edge or tumor center. Frequently, they also resect regions of targeted tissue on the tumor margin that are outside the tumor edge that appear to be grossly normal but are infiltrated by dispersing tumor cells upon histological examination.

The compositions described herein are used in intra-operative imaging (IOI) techniques to guide surgical resection and eliminate the "educated guess" of the location of the tumor by the surgeon. Previous studies have determined that more extensive surgical resection improves patient survival. It was shown that a PSMA-targeted phthalocyanine compound was shown to be easily detectable at real-time imaging exposures (i.e., at <67 ms) and thus capable of being used for real-time IGS during urological surgery. Thus, the compositions described herein for use in image-guided surgery can increase patient survival rates especially when combined with subsequent PDT in accordance with a method described herein.

In some embodiments, IGS can be performed real-time using an in vivo imaging system, such as an intraoperative near-infrared fluorescence imaging system. In certain embodiments, image guided surgery can be performed using a FLARE (Fluorescence-Assisted Resection and Exploration) intraoperative NIR fluorescence imaging system where the targeted cancer is imaged at a wavelength of about 671 nm to about 705 nm. In an exemplary embodiment, the targeted PMSA expressing cancer is imaged during image guided surgical resection at about 700 nm.

Following surgical resection, residual PSMA expressing cancer cells that have penetrated beyond the resection site may revert to a proliferative state to produce a more aggressive recurrent tumor that continues to disperse into nonneoplastic tissue adjacent the resection site and beyond. A therapeutic method described herein can be used to minimize cancer metastasis after a surgical resection procedure targeting PSMA positive cancer cells and/or tumor tissue using photodynamic therapy (PDT).

Therefore, a therapeutic method described herein further includes the step of irradiating the PSMA-targeted phthalocyanine compounds bound to and/or complexed with the PSMA expressing cancer cells remaining in, and/or adjacent to, the surgical site to induce the cytotoxic effects of the phthalocyanine compound on residual cancer cells following surgical resection of the cancer.

Methods for conducting PDT are known in the art. See for example Thierry Patrice. *Photodynamic Therapy*; Royal Society of Chemistry, 2004. PDT is a site specific treatment modality that requires the presence of a photosensitizer, light, and adequate amounts of molecular oxygen to destroy targeted tumors (Grossweiner, Li, The sicence of phototherapy. Springer: The Netherlands, 2005). Upon illumination, a photoactivated sensitizer transfers energy to molecular oxygen that leads to the generation of singlet oxygen ($O^2$) and other reactive oxygen species (ROS), which initiate apoptosis and oxidative damage to cancer cells. Only the cells that are exposed simultaneously to the targeted PDT compound (which is non-toxic in the dark) and light are destroyed while surrounding healthy, non-targeted and non-irradiated cells are spared from photodamage. Furthermore, the fluorescence of the phthalocyanine compound coupled to the PSMA targeting moiety enable simultaneous diagnostic optical imaging that can be used to guide the PDT step of the method of treating cancer described herein.

Following administration and detection/localization of PSMA-targeted phthalocyanine compounds, the targeted cancer cells can be exposed to therapeutic amount of light that causes cancer cell damage and/or suppression of cancer cell growth. The light, which is capable of activating the PDT therapeutic agent can delivered to the targeted cancer cells, using for example, semiconductor laser, dye laser, optical parametric oscillator or the like. It will be appreciated that any source light can be used as long as the light excites the phthalocyanine compound bound or complexed with a PSMA expressing cancer cell.

In some embodiments, the surgical resection site can be irradiated using visible laser diodes to photoactivate the phthalocyanine compound coupled to the PSMA targeting moiety. For example, the surgical resection site can be irradiated using visible laser diodes emitting at 672 nm. In certain embodiments, the surgical resection site can be irradiated with an amount of radiation effective to inhibit tumor recurrence in the subject. In an exemplary embodiment, the PDT step of the method of treating cancer described herein can include irradiating the resection site bed with a 672 nm laser for 12.5 minutes with total radiant exposure of 75 $J/cm^2$.

Following the PDT step of a method of treating cancer described herein, the resection site of a subject can be further imaged and irradiated after a period of time(s) to detect and ablate residual PSMA expressing cancer cells that may have survived previous irradiation. This optional step may or may not include additional administration of a pharmaceutical composition including a PSMA-targeted phthalocyanine compound.

In accordance with the method described herein, pharmaceutical compositions including a PSMA-targeted phthalocyanine compound are administered to a subject to detect and treat a PSMA expressing cancer in subject. One example of a PSMA expressing cancer is a tumor. The tumor can include a solid tumor, such as a solid carcinoma, sarcoma or lymphoma, and/or an aggregate of neoplastic cells. The tumor can include both cancerous and pre-cancerous cells. Exemplary PSMA expressing cancers treated in accordance with a method described herein can include renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. In certain embodiments, the PSMA cancer is a metastatic prostate cancer.

The specific process utilized to administer and detect the PSMA-targeted phthalocyanine compounds of the present invention, and the enhanced results produced by the compounds when used for a combination of image guided surgery and photodynamic therapy, are more particularly described below in the following examples. The following example is for the purpose of illustration only and is not intended to limit the scope of the claims, which are appended hereto.

Example 1

In this Example, we demonstrate a targeted photodynamic agent that can be used for both image-guided surgery (IGS) and adjuvant targeted photodynamic therapy (PDT), allowing better visualization of tumor margins and elimination of residual tumor tissues. This study presents a new treatment option for patients with prostate cancer undergoing surgery, which significantly improves tumor visualization and discrimination during surgery, including identification of cancer in lymph nodes.

Using a prostate specific membrane antigen (PSMA)-targeted PDT agent we previously developed, PSMA-1-Pc413, we showed that PSMA-1-Pc413 selectively highlighted PSMA-expressing tumors, allowing IGS and more complete tumor resection compared with white light surgery. Subsequent PDT further reduced tumor recurrence and extended animal survival significantly. This approach also enabled identification of tumor cells in lymph nodes.

PSMA-1-Pc413 strongly emits near-IR (NIR) light at 678 nm, binds to PSMA-expressing cancer cells, and is able to destroy them when irradiated by NIR light. Due to limitations in light penetration and irradiating all tumor cells, we postulated that it might be more effective to use PSMA-1-

Pc413 as a theranostic combining IGS and PDT to fully ablate nonresected tumor tissues and/or cancer cells. Currently, there are very few examples of IGS followed by PDT, and most of these studies rely on nonspecific or nontargeted uptake of PDT agents into the tumor, e.g., 5-ALA for glioblastoma. No such study has been performed on prostate cancer. In this study, we used PSMA-targeted Pc413 for IGS followed by PDT (FIG. 1A) and found that PSMA-1-Pc413 was able to visualize cancer, enable more complete surgery, and effectively destroy invisible localized microscopic cancer cells by PDT.

Materials and Methods

Cell Culture

Retrovirally transfected PSMA-positive PC3pip cells were obtained from Dr. Michel Sadelain (Memorial-Sloan Kettering Cancer Center, New York, N.Y.). CWR22vr1 cells were obtained from the ATCC. Cells were last checked by Western blot and flow sorted in 2018, and no genetic authentication was performed. *Mycoplasma* test was last performed in 2015. Cells were maintained in RPMI1640 medium with 10% FBS. PC3pip cells were transfected with GFP by lentivirus infection. Cells were discarded after passage 6.

Detection of ROS In Vivo

Animal experiments were approved by the University Institutional Animal Care and Use Committee (#150033). Six- to 8-week-old male athymic nude mice were implanted subcutaneously with $1 \times 10^6$ of PC3pip on the right dorsum. When tumor diameter reached 10 mm, PSMA-1-Pc413 (0.5 mg/kg) was injected i.v. via the tail vein. Twenty-four hours later, mice received 100 nmol of ROSstar800cw (Li-Cor Biosciences) in PBS. Animals were imaged 30 minutes later and then illuminated with 672 nm laser (Applied Optronics Corp) with irradiance of 33.3 mW/cm2 for 25 minutes (total radiant exposure of 150 J/cm2). Fluorescence imaging was performed on a Maestro in vivo Imaging system (Perkin-Elmer): yellow filter for PSMA-1-Pc413 signal (excitation 575-605 nm, emission filter 645 nm longpass); deep red filter for ROSstar800cw (excitation 671-705 nm, emission filter 750 nm longpass). Experiments were repeated in 3 mice.

Detection Sensitivity for PSMA-1-Pc413

PSMA-1-Pc413 and Forte700NHSester (Curadel LLC) were serially diluted in mouse serum and taken up by microcapillary tubes. The tubes were inserted to a cap device with 10 mL sample volume window (Curadel LLC) and imaged at 700 nm (Curadel RP1 Fluorescence Image System) using 100% power and varying exposure. Signals from each capillary tube were quantified using Curadel software.

In Vivo Image of PSMA-1-Pc413 in Orthotopic Mice Model

To establish an orthotopic prostate cancer model, 6- to 8-week old athymic nude mice were first anesthetized by i.p. injection of 50 mg/kg ketamine/xylazine. A transverse incision was made in the lower abdomen to expose the prostate. Ten microliters of PC3pipGFP cells ($5 \times 10^5$) in PBS were injected into the dorsal lateral prostate gland. The incision in the abdominal wall was then closed. After about 4 weeks (tumor diameter approximately 1 cm), mice receive 0.5 mg/kg PSMA-1-Pc413 and were imaged 24 hours later by a Maestro imaging device (yellow filter: PSMA-1-Pc413, excitation 575-605 nm, emission filter 645 nm longpass; and blue filter: GFP, excitation 445-490 nm, emission filter 515 nm long pass). Mice were then euthanized. After the primary tumor was removed to expose the lymph nodes (LN) buried behind the primary tumor, the mouse was again imaged. The resected primary tumor and lymph nodes were fixed in 10% formalin, paraffin embedded, sectioned, and slides prepared. One set of the slides was subjected to hematoxylin and eosin staining, and the adjacent set was observed under a Leica DM4000B fluorescence microscope (Leica Microsystem Inc.) to visualize GFP and PSMA-1-Pc413 fluorescence. Experiments were repeated in 5 mice.

Intramuscle Prostate Tumor Xenograft Model

PSMA-positive PC3pipGFP cells ($1 \times 10^6$) were injected into the muscle of the right leg of 6- to 8-week-old male athymic nude mice. Tumor growth (GFP signal) was monitored twice a week using the Maestro imaging device and calipers. When tumors reached 200 mm$^3$, further studies were performed.

In Vivo Surgery and PDT Treatment of Intramuscle PC3pipGFP Tumors

Mice were randomly divided into three groups: WLS, IGS, and IGS, followed by PDT (IGS+PDT; FIG. 1A). All mice received 0.5 mg/kg PSMA-1-Pc413 via tail vein injection. Surgery was performed at 24 hours after injection for peak accumulation of PSMA-1-Pc413. Before surgery, pre-images for both GFP and PSMA-1-Pc413 were obtained. WLS was performed under room light. For IGS, tumors were removed under the guidance of Curadel RP1 at an exposure (50 ms), which allowed real-time imaging. After surgery, mice were imaged again by Maestro, and then the wounds were sutured for WLS group and IGS group. For the IGS+PDT group of animals, the resection bed was irradiated with 672 nm laser (Applied Optronics Corp) for 12.5 minutes with total radiant exposure of 75 J/cm2. Light was delivered through a GRIN-lens-terminate multimode fiber (OZ Optics) and was adjusted to cover all the surgical area (~1.0-1.5 cm in diameter). After PDT, the mice were imaged by Maestro, and the wounds were sutured. Tumor growth was then monitored by Maestro every other day for 80 days. Mice were terminated when the tumor reached the size of 1.5 cm.

Statistical Analysis

The Student t test was used to compare Maestro signals in different treatment groups. Tumor recurrence and Kaplan-Meier survival data were analyzed by SAS9.4 using exact pairwise Wilcoxon rank-sum test. A P value<0.05 was considered statistically significant for all comparisons.

Results

PSMA-1-Pc413 Generated ROS after PDT

Figure 1B:
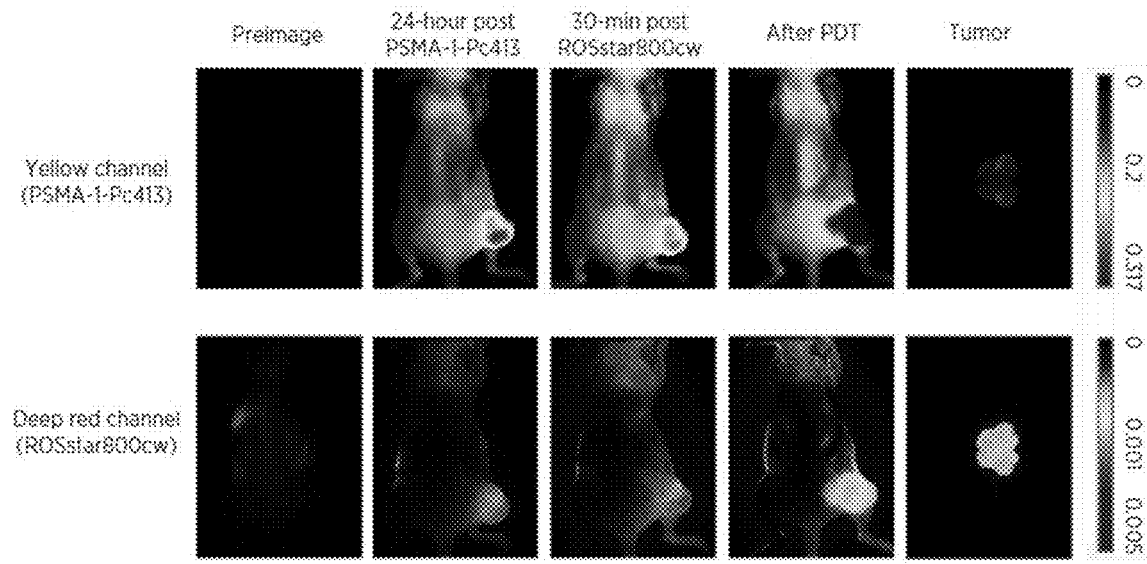
Figure 4A:
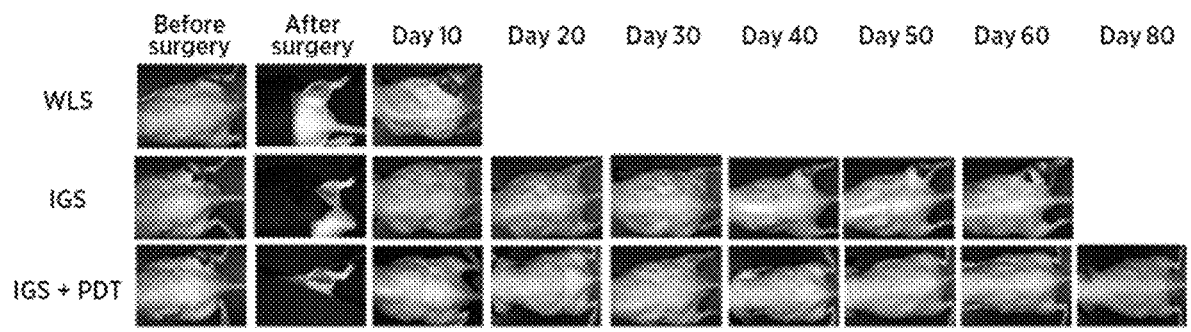
FIGS. 4 (A-C) illustrate a combination of IGS and PDT delayed tumor progression recurrence and extended animal survival. (A) Representative postsurgery monitoring images of mice from WLS, IGS, and TGS+PDT groups measured using Maestro GFP channel. (B) Tumor recurrence curves of mice from three experimental groups (n=animal numbers). IGS did not significantly delay tumor recurrence as compared with WLS (P=0.2222). The tumor recurrence was significantly delayed by IGS+PDT. *, P=0.0008, IGS+PDT vs. WLS; #, P=0.00084, IGS+PDT vs. IGS. (C) Kaplan-Meier survival curves of mice from the three experimental groups. IGS extended the animal survival significantly as compared with WLS (♦, P=0.0317). The survival was further prolonged by PDT.*, P=0.0008, IGS+PDT vs. WLS; #, P=0.0008 IGS+PDT vs. IGS.
Figure 4B:
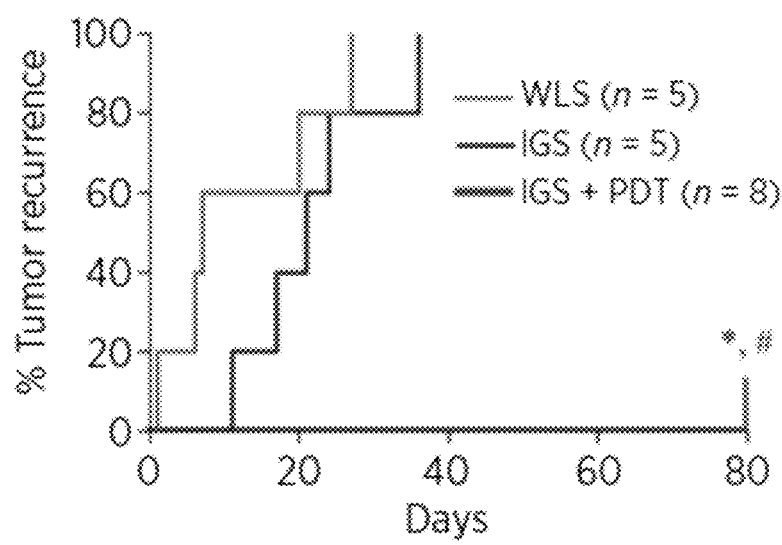
Figure 5:
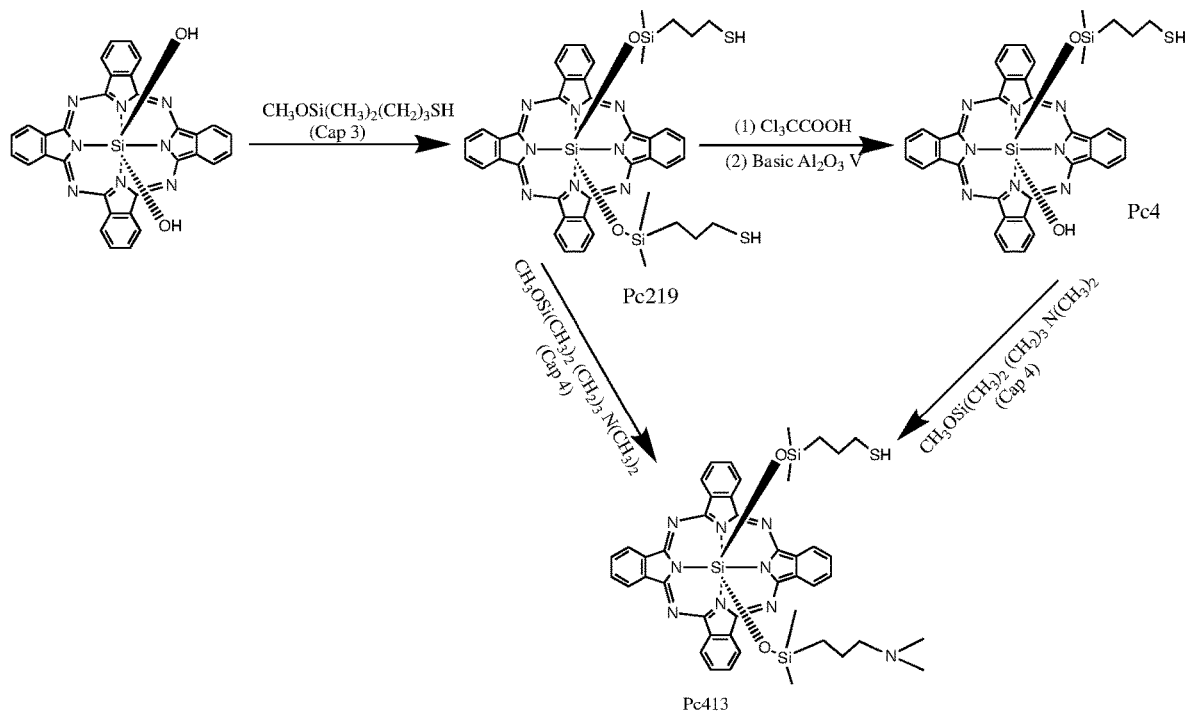
FIG. 5 illustrates a synthesis scheme for Pc413.

To confirm that PSMA-1-Pc413 generates ROS in vivo, its proposed mechanism of action, we used ROSstar800cw conversion into fluorescent cyanine to detect ROS. Before PDT, PSMA-1-Pc413 fluorescent signal was mainly observed in PC3pip tumors (FIG. 1B, top plot, 2nd and 3rd columns) with minimal ROSstar800cw fluorescence observed (FIG. 1B, bottom plot, 2nd and 3rd columns). After PDT, there was a dramatic increase in ROSstar800cw fluorescence, and little PSMA-1-Pc413 signal was observed due to photo activation (FIG. 1B, 4th column). Ex vivo images of the bisected tumor showed that ROS was present throughout the tumor tissues (FIG. 1B, 5$^{th}$ column). To assess IGS sensitivity (i.e., detection limit), we compared PSMA-1-Pc413 fluorescence with Forte700 NHS ester, a typical agent used to derive IGS probes. At 50 ms exposure time, the fluorescent signal from PSMA-1-Pc413 was about 2-fold higher than that from Forte700. At the highest exposure, 10 femtomol of PSMA-1-Pc413 was able to be detected, suggesting that PSMA-1-Pc413 was suitable for IGS when imaged using the Curadel RP1 camera system.

Detection of Primary Tumors and LN Metastasis

Figure 2A:
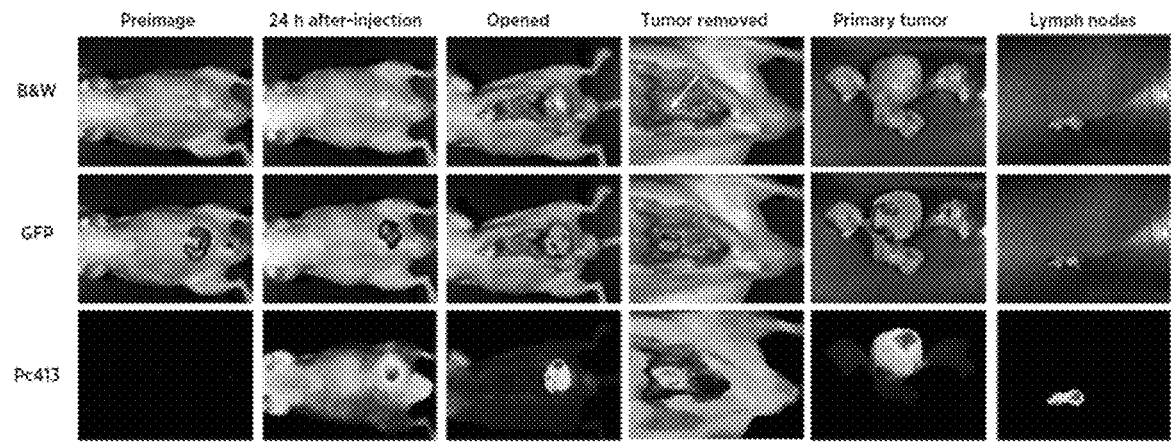
FIGS. 2(A-B) illustrate in vivo fluorescence imaging of mice bearing orthotopic PC3pipGFP tumor. (A) Representative images of whole mouse, primary tumor, and LNs. PSMA-1-Pc413 was able to detect both primary tumor and LN metastasis. White arrow, iliac LNs. Representative images are shown from five animals. (B) Histologic analysis of resected primary tumor and LNs. Presence of tumor cells in LNs was confirmed by GFP signal, PSMA-1-PC413 signal, and hematoxylin and eosin (H&E) staining. White asterisks (*), the rim of lymphocytes in LNs. Red arrows and dashed blue out lines indicate the residual lymphocyte islands in LN surrounded by tumor cells. Images in orange boxes are the enlarged microscopic images of the rectangles in column 1.
Figure 2B:
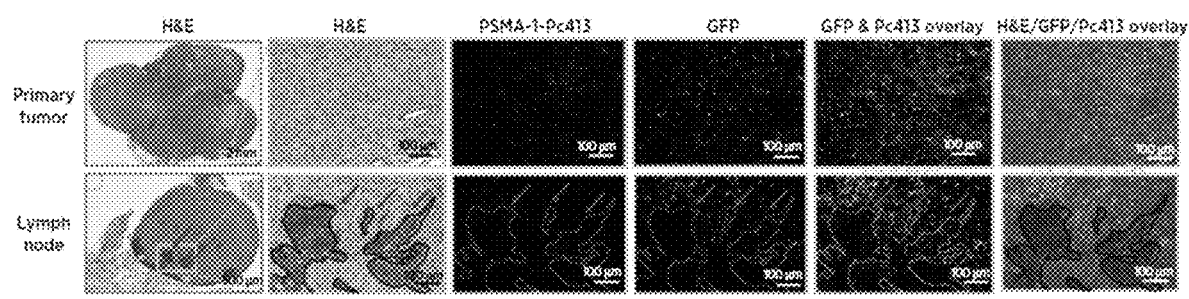

Most deaths from cancer are a result of metastasis. Detection of LN metastases is of major prognostic significance for many cancers. Using an orthotopic human prostate cancer mouse model, reported to develop LN metastases, we tested if PSMA-1-Pc413 has the ability to detect LN metastases. Twenty-four hours after PSMA-1-Pc413 administration, mice bearing orthotopic PC3pipGFP tumors displayed coincident GFP and PC413 fluorescent signals in the primary tumor (FIG. 2A). Removal of the primary tumor revealed enlarged iliac LNs as reported by others. Fluorescence imaging demonstrated coincidence of GFP and PSMA-1-Pc413 fluorescence in the LNs (FIG. 2A). Pathologic analysis demonstrated that both the prostate gland and LNs contained cancer and that the GFP and PSMA-1-Pc413 signals were highly correlated (FIG. 2B), demonstrating that PSMA-1-Pc413 could detect both primary prostate tumor and LN metastases.

IGS Using PSMA-1-Pc413

Figure 3A:
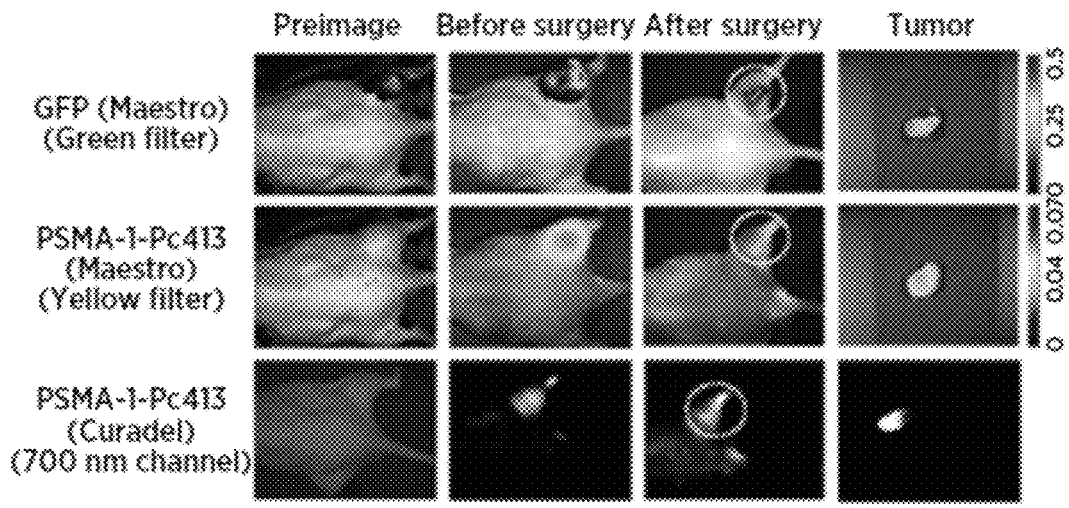
FIGS. 3 (A-D) illustrate the use of PSMA-1-Pc413 for IGS and PDT. (A) Representative images of WLS mice under Maestro and Curadel imaging systems. Circles, surgical bed. (B) Representative images of IGS+PDT mice under Maestro and Curadel imaging systems. Minimal amount of GFP and PSMA-1-Pc413 signals was observed in the wound with loss of PSMA-1-Pc413 signal due to photo activation. Circles, surgical bed. (C) Quantification of GFP signals in the three experimental groups before surgery (left), after surgery (middle), and after IGS+PDT (right). Before surgery, similar GFP signal was observed in three experimental groups before surgery (left). After surgery, significantly lower GFP signal was observed in the IGS and IGS+PDT groups than in the WLS group (*, P<0.05: middle). Values are mean±SD (n=5 animals for WLS and IGS; n=8 for IGS+PDT). (D) Quantification of PSMA-1-Pc413 signals in the experimental groups before surgery (left), after surgery (middle), and after IGS+PDT (right). After surgery, a significant difference was observed between IGS/IGS+PDT and WLS group (middle;*, P>0.05). Within the IGS+PDT group, PDT further reduced PSMA-1-Pc413 signal significantly as compared with after IGS alone (right). Values are mean±SD (n=5 for WLS and IGS, n=8 for IGS+PDT).
Figure 3B:
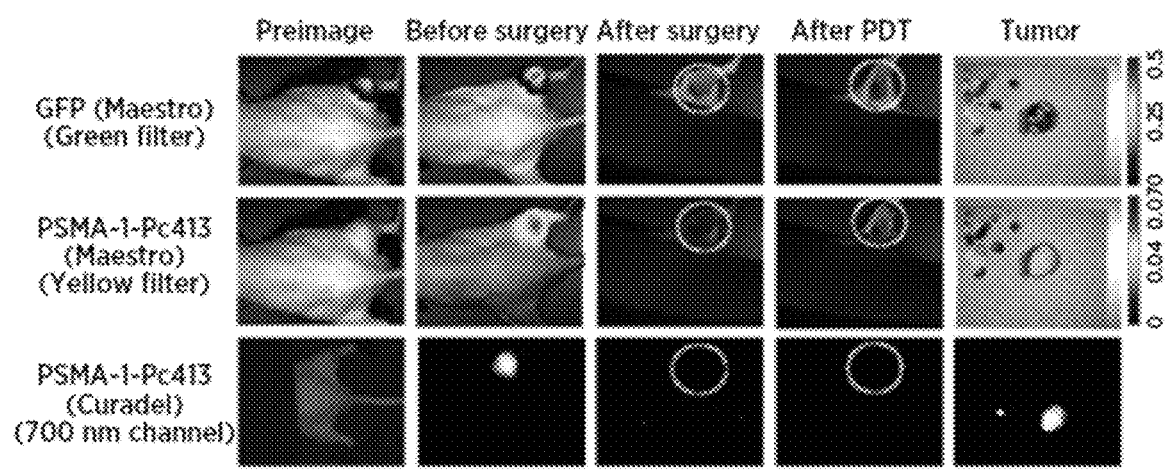
Figure 3C:
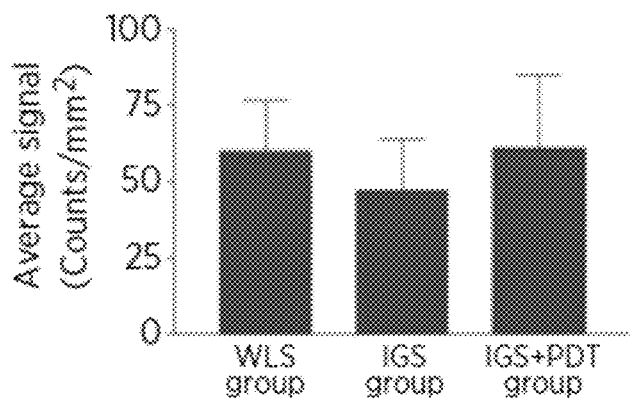
Figure 3C:
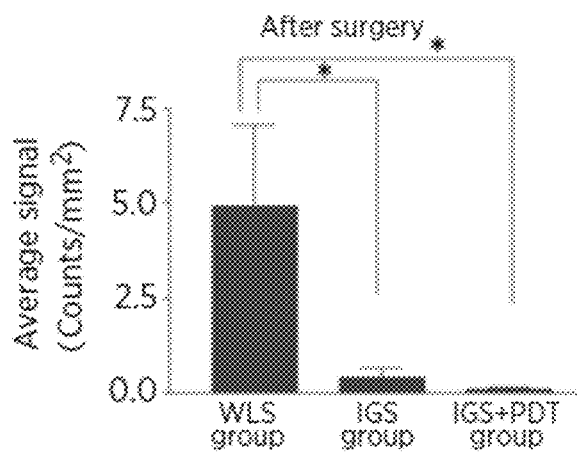
Figure 3C:
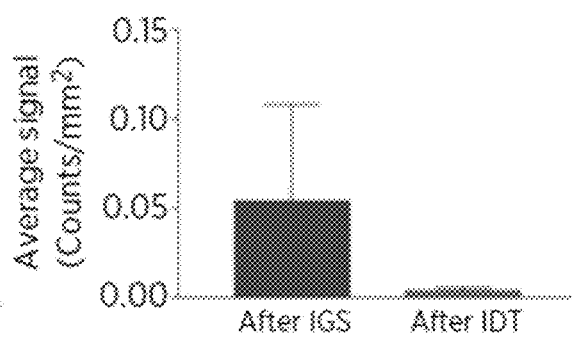
Figure 3D:
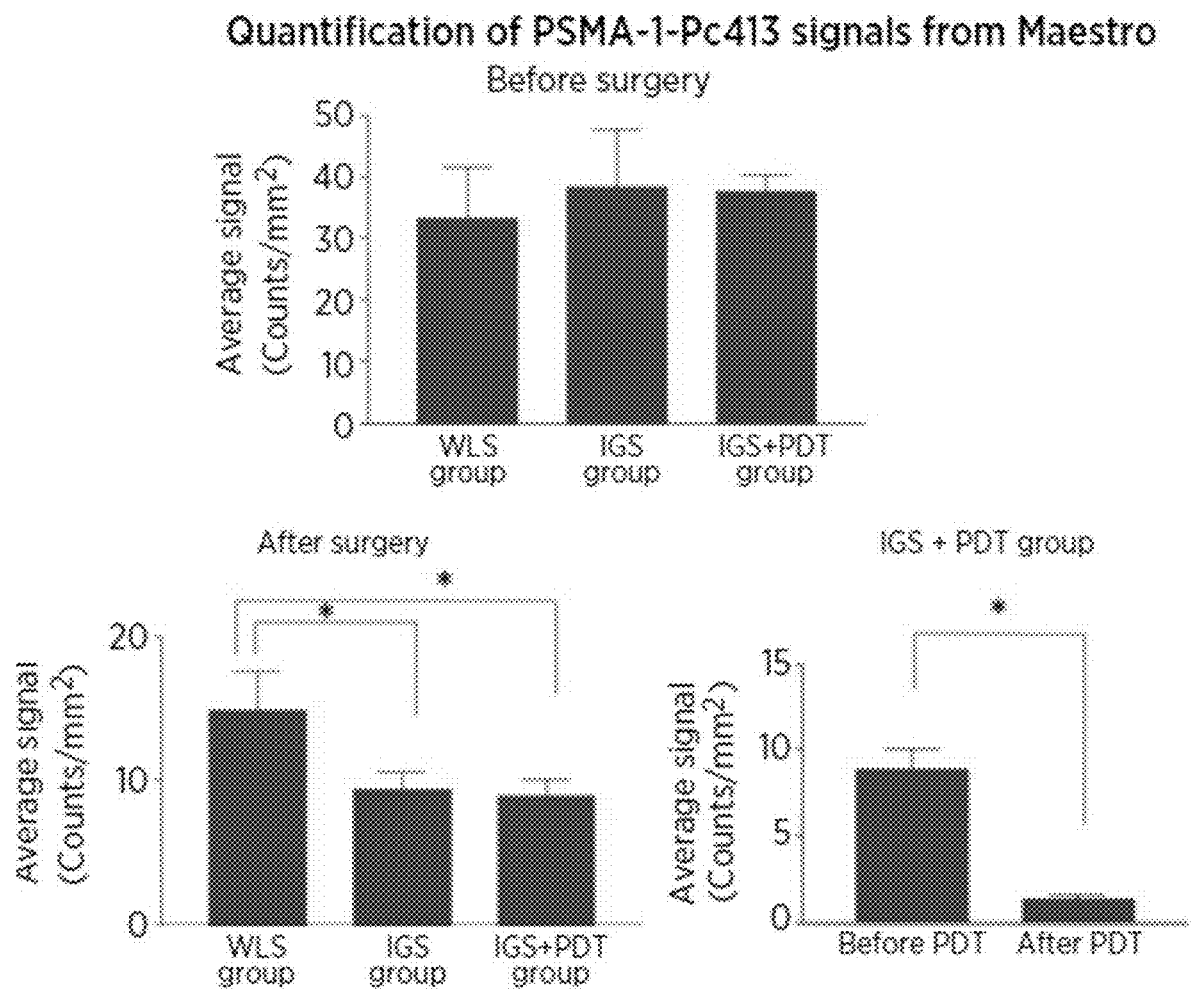

To assess the potential utility of PSMA-1-Pc413 to aid tumor resection and ablation of remaining tumors/cancer cells, we compared animals receiving WLS, IGS, and IGS+PDT (FIG. 1A). Because mouse orthotopic prostate cancer models are not suitable for surgery, we developed an intra-muscle tumor model. The muscular injection site resulted in tumors that were less encapsulated than subcutaneous xenografts, had some tissue infiltration, causing more challenges for surgery. We also demonstrated microdispersions of the cells away from the tumor mass using Cryo-imaging Twenty-four hours after injection probe, coincident fluorescent signal was observed in PC3pipGFP tumors for both GFP and PSMA-1-Pc413 (FIGS. 3A and B, $2^{nd}$ column). Tissue distribution at 24 hours after injection of PSMA-1-Pc413 showed highest uptake in the liver, followed by PC3pip tumor, then kidneys with washout occurring for the organs by 96 hours. Prior to surgery, the GFP and PSMA-1-Pc413 signals had similar intensities in all groups (FIGS. 3C and D, left). Postoperative imaging showed fluorescence remaining in the surgical field for WLS (FIG. 3A, 3rd column) with both GFP and PSMA-1-Pc413, and PSMA-1-Pc413 signal was detectable using the Curadel camera (FIG. 3A, bottom row). When IGS was performed, high fluorescence was observed in the tumor, which helped identify tumor tissues (FIG. 3B, bottom row). Minimal remaining fluorescence (GFP or PSMA-1-Pc413) was observed in mice that underwent IGS (FIG. 3B, 3rd column). Comparison of average fluorescent signals showed that both the GFP and PSMA-1-Pc413 signals (FIGS. 3C and D, middle) were significantly lower in IGS and IGS+PDT groups than those in the WLS group (P<0.05). These results show that IGS was able to highlight tumor tissue not visible during WLS, resulting in more complete tumor removal. Sequential PDT treatment of the IGS surgical wound led to significant reduction in PSMA-1-Pc413 fluorescent signal, indicating PDT was activated in the surgical bed (FIG. 3B, 4th column; FIG. 3D, right). GFP signal in the IGS wound was not significantly reduced after PDT, (FIG. 3C, right). To demonstrate that fluorescence was associated with tumor tissues, a total of 92 pieces of both fluorescing and nonfluorescing tissues resected during IGS and IGS+PDT procedures were collected and underwent blinded pathologic analysis. Among the 92 samples, 22 did not show any fluorescence and were pathologically negative for cancer (true negatives); 68 showed fluorescence and were positive for cancer (true positives); 2 showed fluorescence, but were not cancer (false positives); and there were no false negatives. Analysis demonstrated sensitivity and specificity of 100% and 91.7%, respectively. Histologic and fluorescence microscopic examination of the resected tumor tissue showed that PSMA-1-Pc413 signal corresponded well with the tumor tissue, was able to delineate the borderline between cancer tissue and normal tissue, and was able to identify cancer cells that invaded into normal tissue.

Figure 4C:
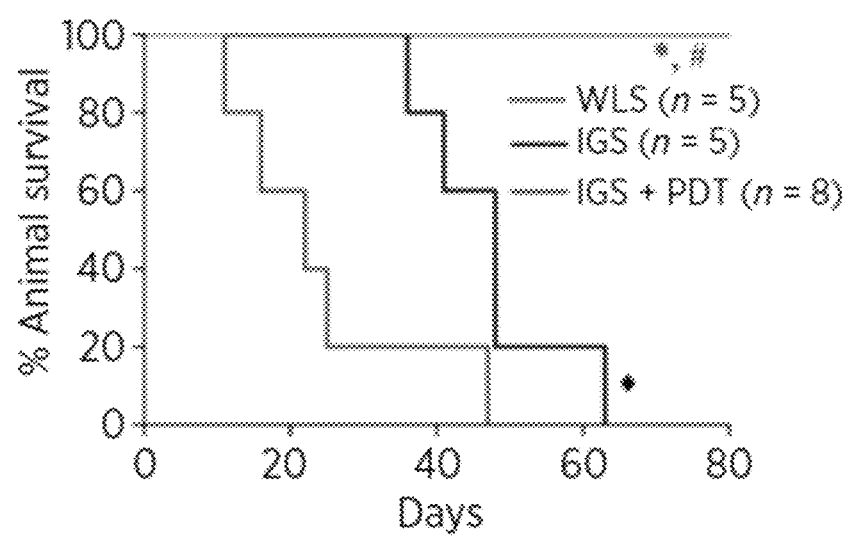

Taken together, these data suggest that the technology may provide precise guidance for surgery. To further confirm that IGS will achieve more complete tumor resection, a separate set of surgeries was performed, after which, the mouse legs with surgical wounds were collected, sectioned, and examined by pathology. It was found that all 5 mice in WLS group had remaining tumor, 3 of 5 mice in IGS group had tumor, and all 4 mice in IGS+PDT group were tumor free. No damage to normal tissues was observed in the IGS+PDT wound beds following PDT PDT in Combination with IGS Reduced Tumor Recurrence After surgery, we next monitored tumor recurrence (GFP signal) and animal survival to evaluate overall response to the theranostic approach. In the WLS group, residual GFP signal was observed after surgery and rapid tumor growth resulted in strong GFP signal by day 10 (FIG. 4A, 1st row). Both IGS and IGS+PDT mice showed no/minimal GFP signal after surgery (FIGS. 3C and 4A). The IGS mice started to show GFP signal on day 36 after surgery (FIGS. 4A and B), but no significant difference was observed in tumor recurrence between WLS and IGS mice (P=0.2222). In contrast, only one mouse in the IGS+PDT group showed tumor recurrence on day 80 after surgery, and the other 7 were tumor free; significant differences were observed between IGS+PDT versus IGS (P=0.00084), and IGS+PDT versus WLS (P=0.0008; FIGS. 4A and B). IGS significantly extended animal survival compared with WLS (P=0.0317), and IGS+PDT further prolonged animal survival to >80 days (P=0.0008 compared with WLS and P=0.0008 compared with IGS, FIG. 4C). No adverse effects or delay in healing was observed in IGS+PDT animals as compared with WLS and IGS animals. We also performed studies using mice bearing prostate tumors derived from human CWR22rv1 cells, which spontaneously overexpress PSMA at a level only 1/12 of that in PC3pip cells. Despite the lower PSMA expression, the level of PSMA-1-Pc413 uptake in CWR22rv1 cells was about 50% of that in the PC3pip tumors and PDT effectively inhibited tumor growth without surgical intervention. When CWR22rv1 tumors were implanted into mouse flank muscles, PSMA-1-Pc413 fluorescent signal was clearly visible and suitable for IGS. IGS+PDT again significantly delayed tumor recurrence and extended animal survival as compared with WLS and IGS groups.

PDT has been used for selective identification and treatment of cancers. Postsurgical photoimmunotherapy (PIT) has shown inhibition of tumor recurrence after surgical resection of pancreatic and head and neck cancer models. However, the ability of PIT to aid IGS in the treatment of prostate cancer has not been explored. Further, these antibody agents are significantly more expensive to make than the small urea/peptide based agent used here, and antibody's longer circulation time could lead to off target accumulation. Although there are a few examples of IGS followed by nontargeted PDT, there are none for prostate cancer, which has 20% to 40% local recurrence that is associated with incomplete surgery. Even in the few examples where IGS was followed by PDT for other cancers, the molecules are not as selective or designed to exploit distinct biochemical biomarkers for the disease targeted and therefore likely may have significant off-target effects and increased toxicity. We have developed a completely novel PSMA-targeted PDT agent to directly exploit overexpression of a biomarker on the surface of most prostate cancers (>95% overexpression). We initially tested this agent as a PDT agent only, i.e., without prior surgery, and demonstrated that primary tumors (Tstage) could be eradicated, but in all cases recurred. Here, we test the hypothesis that recurrence of primary tumors after PDT treatment is not complete because the tumor burden is too large for PDT to effectively "get" all the tumor cells. We hypothesized that IGS will reduce tumor burden and, followed immediately by PDT, improve survival. We showed that PSMA-1-Pc413 is easily detectable at realtime imaging exposures (<67 ms) and can provide real-time IGS for urological surgeons. It was noticed that tumor depths obscured some GFP signal when imaged in vivo, but in all cases when tumors were excised, there was a good correlation between tumor GFP expression and PSMA-1-Pc413 fluorescence.

Surgery is the main treatment option for primary prostate cancer. In our novel approach, surgical resection was improved by PSMA-1-Pc413 IGS and, when immediately followed by PDT, significantly improved outcome. The combined approach resulted in a local tumor recurrence rate of only 1 of 8 animals, first detectable 80 days after completion of the procedure, i.e., IGS+PDT (theranostic) cures prostate cancer 87.5% of the time. Cryo-image of the tumor-bearing mice showed microdispersion of cancer cells away from the primary tumor mass, underscoring the prudence of the hypothesis and the importance of adjuvant PDT treatment. Pathology showed a good correlation between tumor remaining in the wound bed and tumor recurrence. IGS+PDT did not damage surrounding normal tissues. Pathology studies of resected tissues showed that the fluorescent tissue pieces resected during IGS were largely cancerous, achieving a sensitivity of 100% and specificity of 91.7%, respectively. It is unclear why the specificity was only 91.7%, given the selectivity of the PSMA-1-Pc413 molecules and the selective expression of the receptor. It is possible that the tissues that were false positive perhaps had significant background fluorescence due to occasional wounds inflicted on the animals by each other. Even though PC3pip cells were engineered to overexpress the PSMA receptor, we used them for these studies because (i) they grow much more rapidly in mice than other prostate cancer cell lines and (ii) express levels of PSMA similar to many prostate cancer cells lines that have not been engineered to overexpress PSMA. We repeated studies with CWR22rv1 cells and demonstrated that the lower expression of PSMA in CWR22rv1 tumors does not significantly affect the utility of the approach to remove residual tumor tissue with PDT following surgery. Interestingly, the Western blot measurements of receptor levels suggest that lower PSMA levels on CWR22rv1 cells can still load cells with substantial level of the PSMA-1-PC413 molecule in vivo. More studies are underway to determine the reason(s) for these differences. Nevertheless, the lower levels of PSMA receptor levels are suitable for IGS+PDT approach. It has been reported recently that low-level PSMA expression is enough for tumor targeting and imaging, which supported our findings. Further, PSMA-1-Pc413 was able to detect LN metastases (FIG. 2).

In conclusion, application of combined IGS and PDT technologies may be able to improve clinical treatment of prostate cancer for patients that elect to undergo radical prostatectomy. It will improve cancer tissue visualization and enable discrimination among cancerous, normal, neural, and muscle cells and tissues during surgery and has the ability to help visualize LN metastases. In particular, the PDT component of the developed theranostic probe provides an adjuvant therapeutic approach to destroy unresectable tissues and/or missed cancer cells, reducing the frequency of positive margins and cancer recurrence. The technology is novel, innovative, and has great potential to be translated into the clinic benefiting patients with prostate cancer but will require outcome studies in addition to decreasing positive tumor margins.

Example 2

Figure 7:
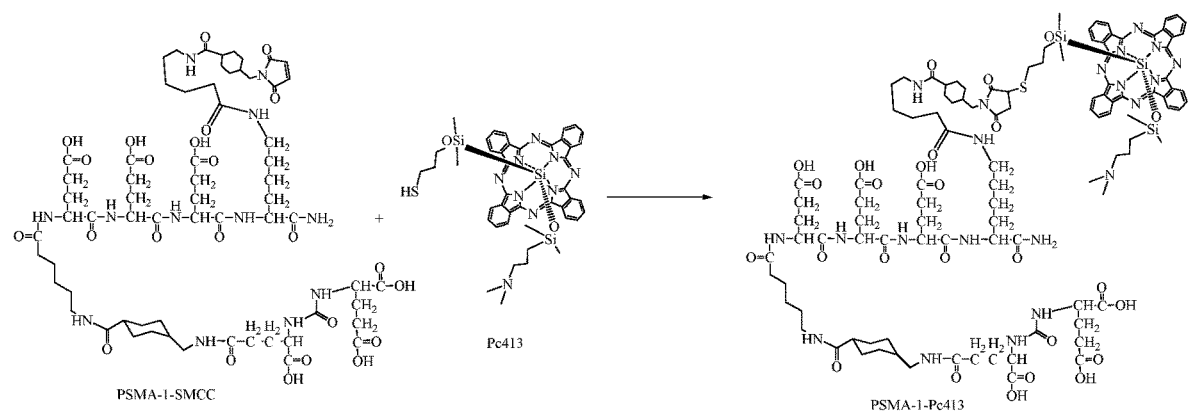
FIG. 7 illustrates a synthesis scheme for PSMA-1-Pc413.

In this Example, we describe the synthesis of a peptide-based, highly negatively charged PSMA ligand (PSMA-1) for PSMA-targeted imaging of prostate cancer, synthesis of Pc413 (FIG. 5), and a PSMA-1 based PDT conjugate PSMA-1-Pc413 (FIG. 7).

Synthesis of Pc 413 (FIG. 5)

Preparation of CH3OSi(CH3)2(CH2)3SH (Cap3)

Under Ar, a 0° C. solution of 3-mercaptopropyltrimethoxysilane(8.5 g) and tetrahydrofuran (50 mL) was treated dropwise with a CH3MgCl-tetrahydrofuran solution (50 mL). The reaction mixture was stirred for 1 h and then treated dropwise with $CH_3OH$ (40 mL), both being done at low temperature (0° C.), diluted with a tetrahydrofuran-diethyl ether solution (1:8, 90 mL), and filtered. The solid was washed (diethyl ether), and the washings and filtrate were combined and concentrated by rotary evaporation at room temperature. The concentrate was distilled (60 torr, 90-110° C.) and weighed (3.8 g, 54%). $^1$H NMR ($C_6D_6$): d 3.21 (s, $^3$H, $OCH_3$), 2.24 (q, $^2$H, $Si(CH_2)_2CH_2$), 1.49 (m, $^2$H, $SiCH_2CH_2$), 1.14 (t, $^1$H, SH), 0.47 (m, $^2$H, $SiCH_2$), 0.04 (s, $^6$H, $SiCH^3$) Cap 3 is a colorless liquid.

Preparation of SiPc[OSi(CH3)2(CH2)3SH]2 (Pc93)

Under Ar, a mixture of SiPc(OH)2 (135 mg, Sigma-Aldrich), cap 3 (1.60 g), and pyridine (80 mL) was distilled (5 mL of distillate) for 1 h, and evaporated to dryness by rotary evaporation (30° C.). The solid was chromatographed (basic-$Al_2O_3$ III, $CH_2Cl_2$-ethyl acetate solution, 5:1), air-dried, and weighed (190 mg, 96%). UV-Vis (toluene) kmax, nm: 669. $^1$H NMR ($C_6D_6$): d 9.72 (m, $^8$H, 1, 4-Pc H), 7.87 (m, $^8$H, 2, 3-Pc H), 0.91 (q, $^4$H, $Si(CH_2)_2CH_2$), 0.39 (t, $^2$H, SH),) 1.02 (m, $^4$H, $SiCH_2CH_2$,) 2.22 (t, $^4$H, $SiCH_2$), ) 2.68 (s, $^{12}$H, $SiCH_3$). $^{13}$C NMR ($CDCl_3$): d 148.9 (5-Pc C), 136.3 (4a-Pc C), 131.1 (2, 3-Pc C), 123.9 (1, 4-Pc C), 28.1 ($Si(CH_2)_2CH_2$), 27.0 ($SiCH_2CH_2$), 15.3 ($SiCH_2$),) 3.2 ($SiCH_3$). Pc 93 is a blue solid. It is soluble in $CH_2Cl_2$, dimethylformamide and toluene, and insoluble in hexanes.

Preparation of HOSiPcOSi(CH3)2(CH2)3SH (Pc219)

A mixture of phthalocyanine Pc 93 (114 mg) and a solution of trichloroacetic acid (150 mg) in $CH_2Cl_2$ (100 mL) was stirred at room temperature for 1.5 h, treated with pyridine (20 mL) and then H2O (100 mL), and separated. The aqueous portion of the reaction product was washed ($CH_2Cl$=), and the washings and the organic portion of the reaction product were combined and concentrated by rotary evaporation (room temperature). The concentrate was passed down an $Al_2O_3$ column (basic-Al2O3V, CH2Cl2-ethyl acetate solution, 10:1), and evaporated to dryness by rotary evaporation (room temperature). The solid was washed (acetonitrile), air-dried and weighed (52 mg, 50%). UV-Vis (toluene) kmax, nm: 680. $^1$H NMR ($C_6D_6$): d 9.67 (m, $^8$H, 1, 4-Pc H), 7.84 (m, $^8$H, 2, 3-Pc H), 0.90 (q, $^2$H, Si(CH$_2$)$_2$CH$_2$), 0.36 (t, $^1$H, SH),) 1.00 (m, $^2$H, SiCH$_2$CH$_2$,) 2.19 (t, $^2$H, SiCH$_2$),) 2.64 (s, $^6$H, SiCH$_3$). $^{13}$C NMR (CDCl$_3$): 149.9 (5-Pc C), 135.8 (4aPc, C), 131.6 (2, 3-Pc, C), 124.2 (1, 4-Pc, C), 27.0 (Si(CH2)2CH2), 26.8 (SiCH$_2$CH$_2$), 15.0 (SiCH$_2$),) 3.2 (SiCH$_3$). HRMS-MALDI (m/z): [M-OH]+calcd for C$_{37}$H$_{29}$N$_8$OSSi$_2$, 689.1724; found 689.1690. Pc 219 is a blue solid. It is soluble in CH$_2$Cl$_2$, dimethylformamide and toluene, and insoluble in hexanes.

Preparation of CH$_3$OSi(CH$_3$)$_2$(CH$_2$)$_3$N(CH$_3$)$_2$ (Cap 4)

Under argon gas a solution of CH3MgCl in tetrahydrofuran (3.0 M, 45 mL) was added dropwise to a cool (ice bath) solution of (CH$_3$O)$_3$Si(CH$_2$)$_3$N(CH$_3$)$_2$ (11 mL) in tetrahydrofuran (100 mL), and the resulting suspension was stirred for 2 hours while being kept cool at about 5° C.). Methanol (20 mL) then was added to the suspension and the mixture formed was filtered. The solid was washed with ether (50 mL) and the washings and filtrate were combined and concentrated with a rotary evaporator (45° C.). The concentrate was fractionally distilled under vacuum (45 torr) and a selected fraction (86-88° C., 5.0 g) was retained (55%): NMR (CDCl$_3$) δ 3.42 (s, CH$_3$O), 2.24 (m, γ-CH$_2$), 2.20 (s, NCH$_3$), 1.49 (m, β-CH$_2$), 0.57 (m, α-CH$_2$), 0.10 (s, CH$_3$Si). The compound is a colorless liquid.

Preparation of HS(CH$_2$)$_3$Si(CH$_3$)$_2$OSiPcOSi(CH$_3$)$_2$(CH$_2$)$_3$N(CH$_3$)$_2$ (Pc 413)

A mixture of Pc 219 (96 mg, 0.14 mmol), cap 4 (37 mg, 0.21 mmol), and pyridine (40 mL) was slowly refluxed for 1 hr (distillate 15 mL) under N2, and concentrated by rotary evaporation (8 torr, room temperature). The solid was chromatographed (basic Al$_2$O$_3$ (Ill), CH2Cl2:ethyl acetate, 5:1), evaporated to dryness by rotary evaporation (room temperature), vacuum dried (room temperature), and weighed (42 mg, 0.049 mmol, 35%).

Alternatively, a mixture of Pc 93 (144 mg, 0.17 mmol), cap 4 (218 mg, 0.21 mmol), and pyridine (50 mL) was slowly refluxed for 1 hr (distillate 20 mL) under N2, and concentrated by rotary evaporation (8 torr, room temperature). The solid was chromatographed (basic Al$_2$O$_3$ (III), CH$_2$Cl$_2$:ethyl acetate, 5:1), evaporated to dryness by rotary evaporation (room temperature), vacuum dried (room temperature), and weighed (58 mg, 0.068 mmol, 40%).

Synthesis of PSMA-1-Pc413

Synthesis of PSMA-1 Liqand

PSMA-1 was synthesized manually using standard Fmoc chemistry. Generally, peptide was synthesized at 0.2 mmol scale starting from C-terminal Fmoc-rink amide MBHA resin. Fmoc-deprotection at each cycle was carried out using 20% piperidine in DMF. Coupling reactions were carried out using 3.3 equiv of Fmoc-amino acids in DMF activated with 3.3 equiv of HCTU and 5 equiv of diisopropylethylamine (DIPEA) in DMF. These steps were repeated each time with an amino acid added. After the peptide sequence Fmoc-Glu'-Amc-Ahx-Glu-Glu-Glu-Lys(Mtt) was built on the resin, the Fmoc group of N-terminal amino acid Glu' was deprotected by 20% piperidine. Then, a chloroform solution containing 3 eq. of H-Glu(OtBu)-OtBu mixed with 2.5 eq. of DIPEA were prepared. The solution is then added slowly to 0.25 eq. triphosgene in chloroform over 10 minutes at room temperature. After a 15-minute incubation, the reaction mixture was mixed with Glu'-Amc-Ahx-Glu-Glu-Glu-Lys on rink amide resin pre-swollen in chloroform with 2.5 eq. of DIPEA. After the reaction was complete, the resin was washed with DMF and then dichloromethane and dried. The peptide was cleaved from resin by TFA/water/triisopropylsilane (950:25:25). The cleaved peptide was purified by preparative HPLC. The products were ascertained by high resolution matrix-assisted laser desorption/ionization mass (MALDI-MS) spectra from an Applied Biosystem 4800 MALDI TOF/TOF Analyzer using positive ion mode. Retention time: 18.6 min. MALDI MS: C$_{48}$H$_{74}$N$_{10}$O$_{20}$, 1087.5 (found); 1087.1 (calculated).

Figure 6:
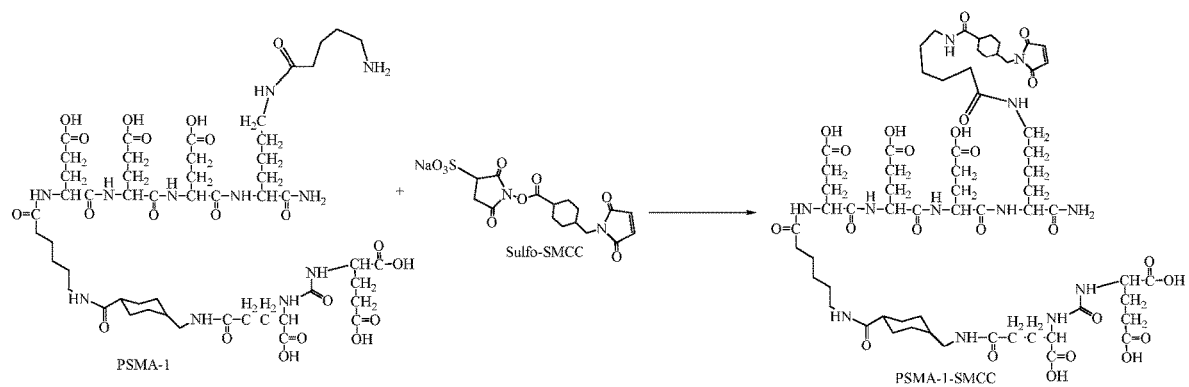
FIG. 6 illustrates a synthesis scheme for PSMA-1-SMCC.

Synthesis of PSMA-1-SMCC (FIG. 6)

Coupling of PSMA-1 to sulfosuccinimidyl-4-(Nmaleimidomethyl)cyclohexane-1-carboxylate (sulfo-SMCC) (Thermo Scientific) was performed in 100 mM phosphate buffer, pH 7.0. PSMA-1 (200 nmol) was dissolved in 100 µL of phosphate buffer; then 400 nmol of sulfo-SMCC in 500 µL of phosphate buffer was added. The reaction mixture was left at room temperature overnight. The crude product was purified by preparative HPLC. Yield: 78%. Retention time: 24.8 min. MALDI-MS: C$_{58}$H$_{87}$N$_{11}$O$_{23}$, 1306.7 (found); 1306.4 (calculated). PSMA-1-SMCC can also be synthesized on the resin by removing the MTT group from the lysine, then have the free NH2 couple to SMCC.

Synthesis of PSMA-1-Pc413 (FIG. 7)

Pc413 (8 mg, 0.01 mmol) was first dissolved in 1 mL of DMF, then PSMA-1-SMCC (0.007 mmol) in 100 µL of 100 mM phosphate buffer, pH 8.0 was added. The reaction mixture was stirred at room temperature for 2 hours and purified by preparative HPLC to get purified PSMA-1-Pc413. Yield: 63%. Retention time: 15.4 min. MALDI-MS: C$_{102}$H$_{134}$N$_{20}$O$_{25}$SSi$_3$, 1996.9 (found, M-C$_7$H$_{19}$NOSi); 1996.3 (calculated).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method for treating a PSMA expressing cancer comprising:

(a) administering systemically to a subject with PSMA expressing cancer a therapeutically effective amount of a pharmaceutical composition, the pharmaceutical composition comprising a PSMA-targeted phthalocyanine compound having formula (I):

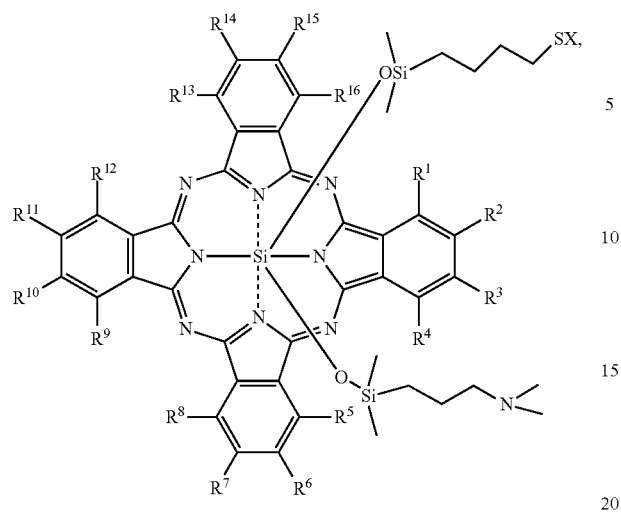
wherein X is a PSMA ligand selected from the group consisting of
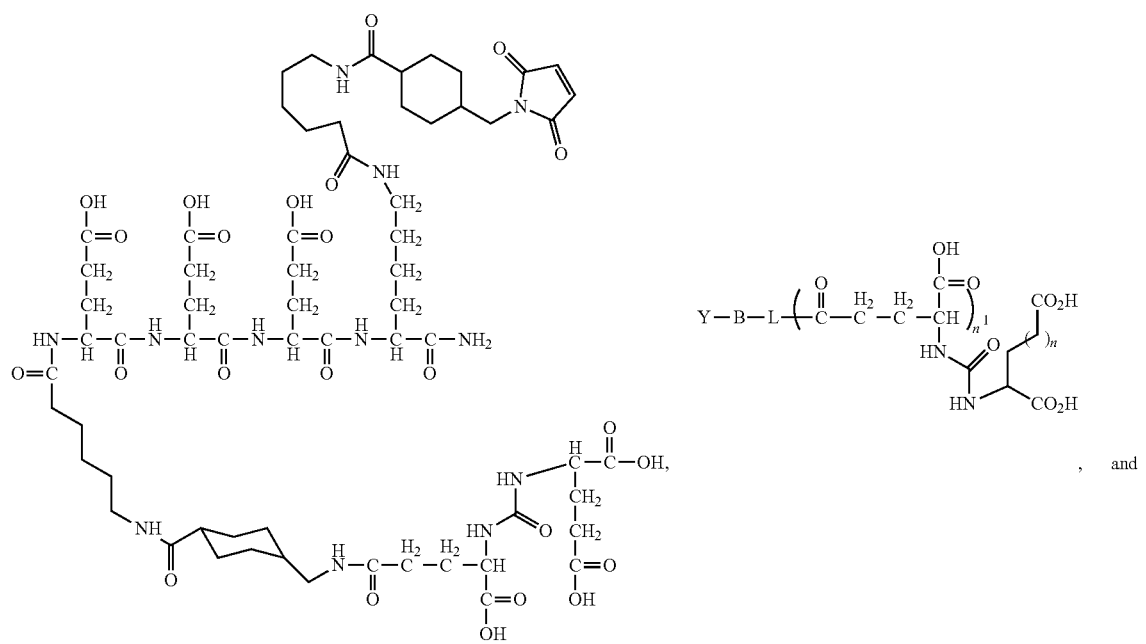
, and -continued

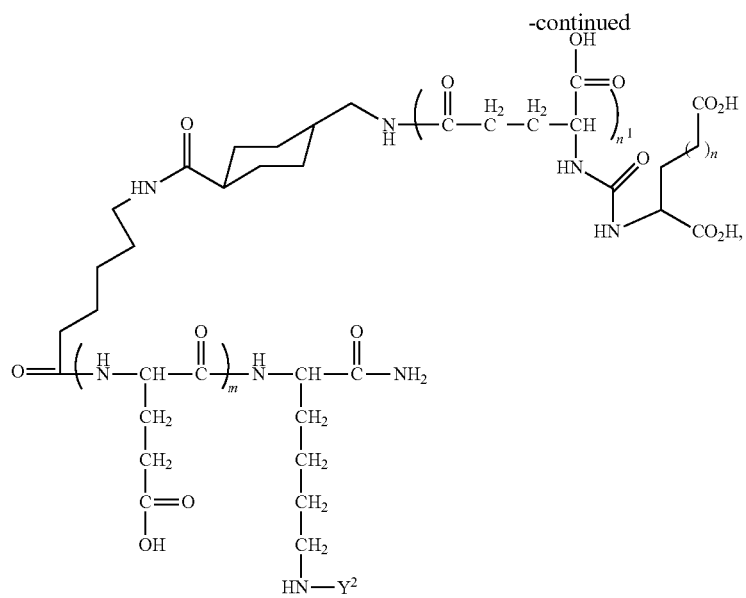

wherein m, n and $n^1$ are each independently 1, 2, 3, or 4;
L is an optionally substituted aliphatic or heteroaliphatic linking group;
B comprises at least one negatively charged amino acid, and
Y and $Y^2$ are the phthalocyanine compound of formula (I) that is directly or indirectly linked or coupled to B;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof;
(b) detecting the PSMA-targeted phthalocyanine compound bound to and/or complexed with cancer cells to determine the location and/or distribution of the cancer cells in the subject;
(c) surgically resecting the cancer in the subject, wherein the detected PSMA-targeted phthalocyanine compound bound to and/or complexed with the cancer cells guide surgical resection of the cancer; and
(d) irradiating the PSMA-targeted phthalocyanine compound bound to and/or complexed with residual cancer cells in the subject following surgical resection.

2. The method of claim 1, wherein $R^1$-$R^{16}$ of the phthalocyanine compound are independently selected from the group consisting of hydrogen, halogen, nitro, cyano, hydroxyl, thiol, amino, and methyl.

3. The method of claim 1, the PSMA ligand comprising a PSMA-1 ligand.

4. The method of claim 1, wherein intra-operative imaging (IOI) of the PSMA-targeted phthalocyanine compound bound to and/or complexed with the cancer cells defines a tumor margin in the subject to guide surgical resection of the cancer.

5. The method of claim 1, the phthalocyanine compound having formula (II):

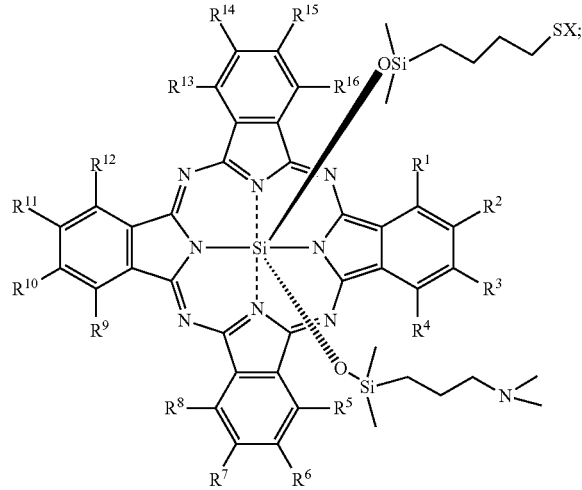

wherein X is a PSMA ligand selected from the group consisting of

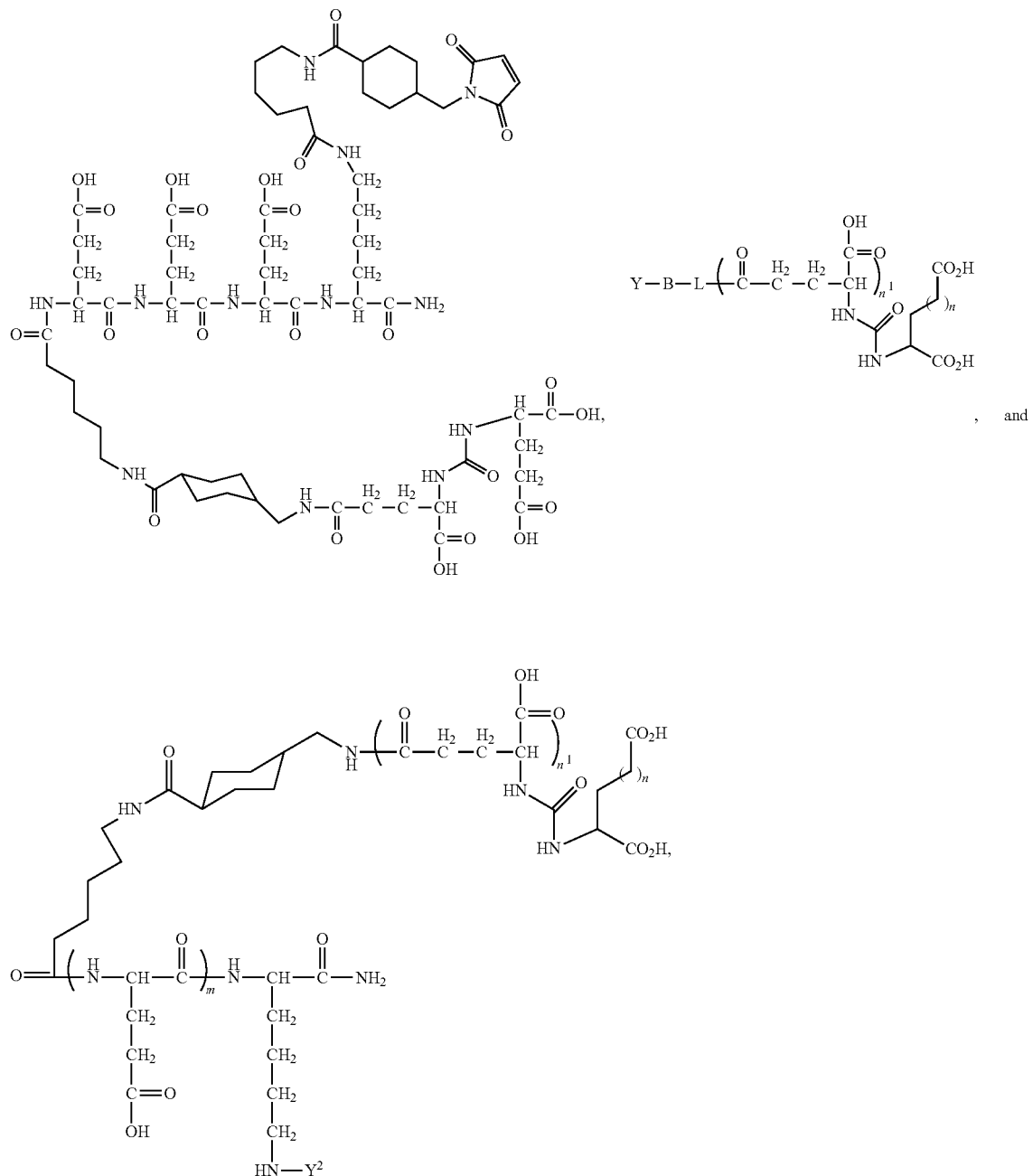

wherein m, n and $n^1$ are each independently 1, 2, 3, or 4;

L is an optionally substituted aliphatic or heteroaliphatic linking group;

B comprises at least one negatively charged amino acid, and

Y and $Y^2$ are the phthalocyanine compound of formula (I) that is directly or indirectly linked or coupled to B;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

6. The method of claim 5, wherein $R^1$-$R^{16}$ of the phthalocyanine compound are independently selected from the group consisting of hydrogen, halogen, nitro, cyano, hydroxyl, thiol, amino, and methyl.

7. The method of claim 1, the phthalocyanine compound having formula (III):
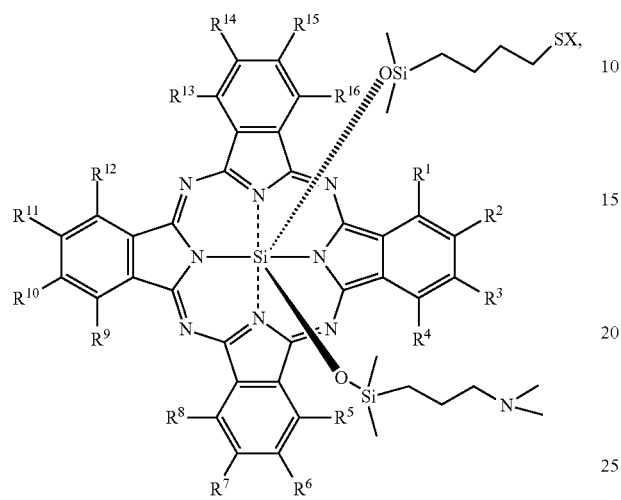
wherein X is a PSMA ligand selected from the group consisting of
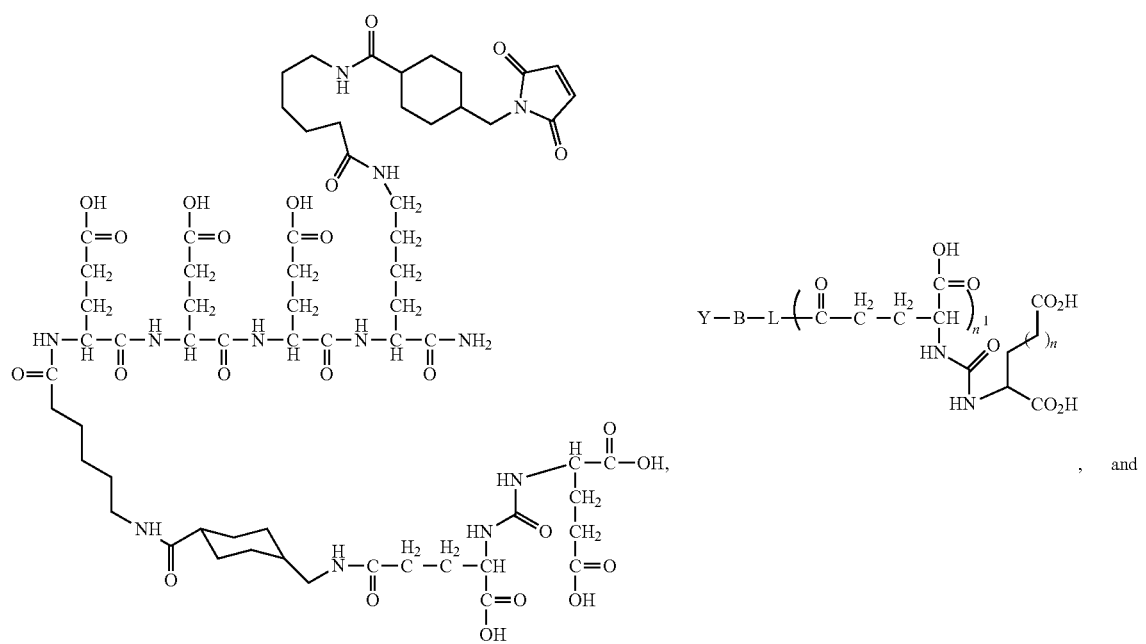

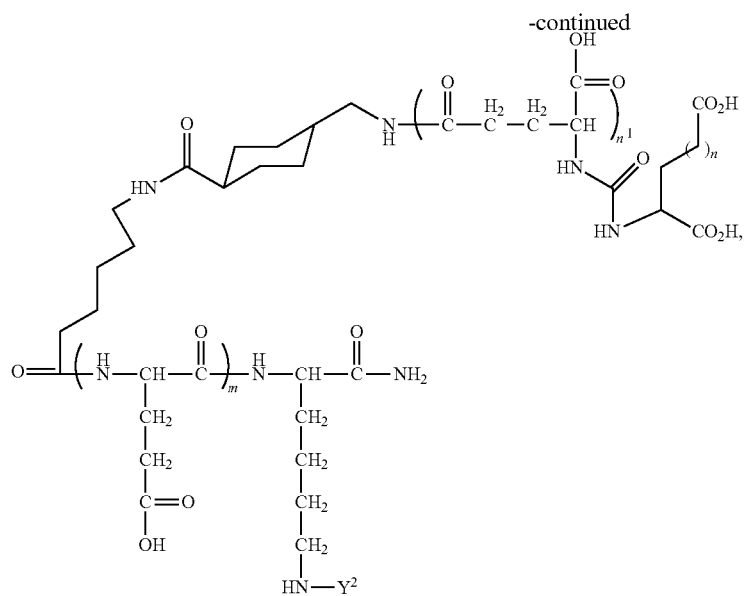

wherein m, n and $n^1$ are each independently 1, 2, 3, or 4;

L is an optionally substituted aliphatic or heteroaliphatic linking group;

B comprises at least one negatively charged amino acid, and

Y and $Y^2$ are the phthalocyanine compound of formula (I) that is directly or indirectly linked or coupled to B;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

8. The method of claim 7, wherein $R^1$-$R^{16}$ of the phthalocyanine compound are independently selected from the group consisting of hydrogen, halogen, nitro, cyano, hydroxyl, thiol, amino, and methyl.

9. The method of claim 1, the phthalocyanine compound having formula (IV):

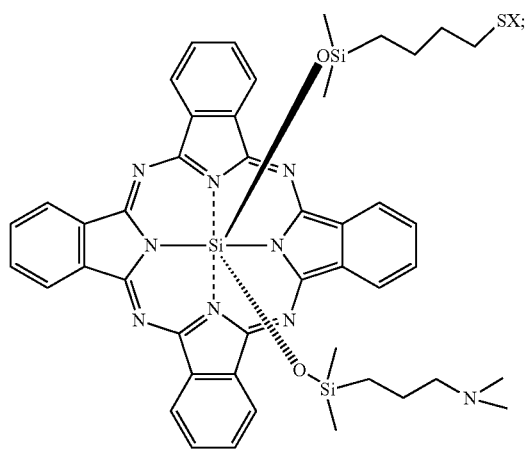

wherein X is a PSMA-1 ligand selected from the group consisting of

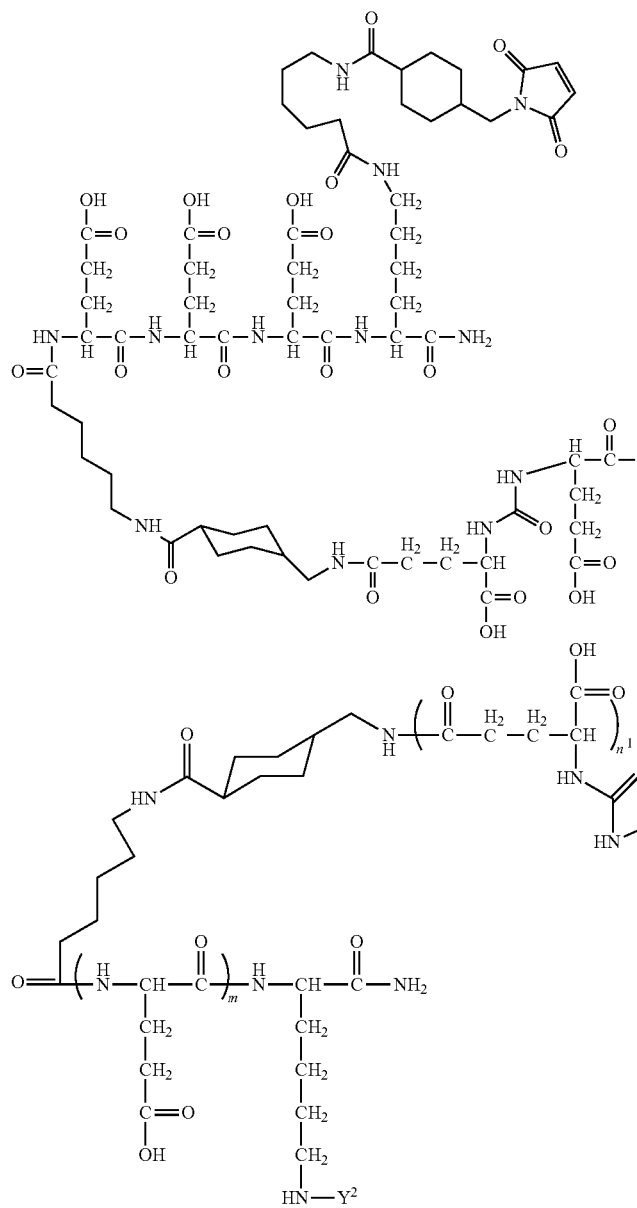

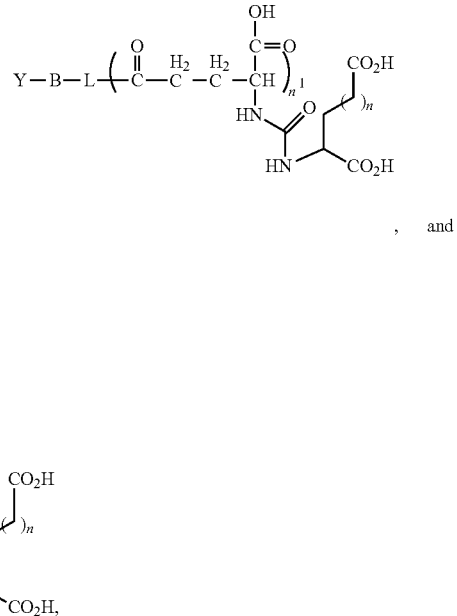

, and wherein m, n and $n^1$ are each independently 1, 2, 3, or 4;
L is an optionally substituted aliphatic or heteroaliphatic linking group;
B comprises at least one negatively charged amino acid, and
Y and $Y^2$ are the phthalocyanine compound of formula (I) that is directly or indirectly linked or coupled to B; and pharmaceutically acceptable salts thereof.

10. The method of claim 1, wherein the PSMA targeted phthalocyanine compound is administered by intravenous injection.

11. The method of claim 1, wherein the PSMA targeted phthalocyanine compound is formulated in a pharmaceutically acceptable carrier.

12. The method of claim 1, wherein the PSMA expressing cancer is selected from the group consisting of renal carcinoma, transitional cell carcinoma of the urinary bladder, testicular embryonal carcinoma, colonic adenocarcinoma, neuroendocrine carcinoma, glioblastoma multiforme, malignant melanoma, pancreatic ductal carcinoma, non-small cell lung carcinoma, soft tissue carcinoma, breast carcinoma, and prostatic adenocarcinoma.

13. The method of claim 12, wherein the cancer is metastatic prostate cancer.

14. The method of claim 1, wherein the residual cancer cells in the subject following surgical resection are irradiated with an amount of radiation effective to reduce tumor growth in the subject.

15. A method for treating a prostate cancer comprising:
(a) administering systemically to a subject with prostate cancer a therapeutically effective amount of a pharmaceutical composition, the pharmaceutical composition comprising a phthalocyanine compound having formula (I):

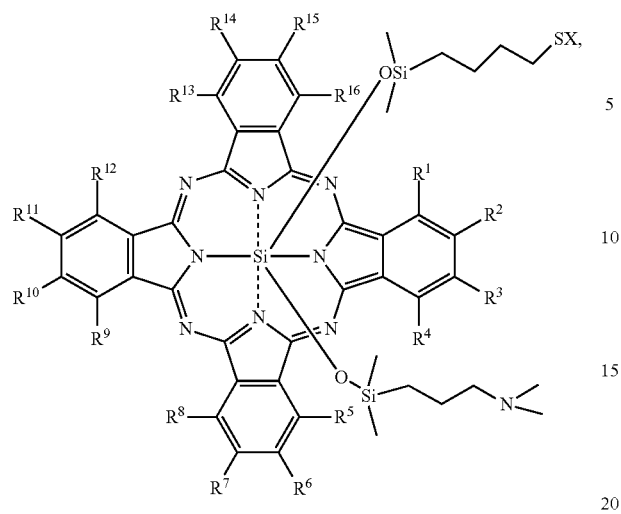
wherein X is a PSMA ligand selected from the group consisting of
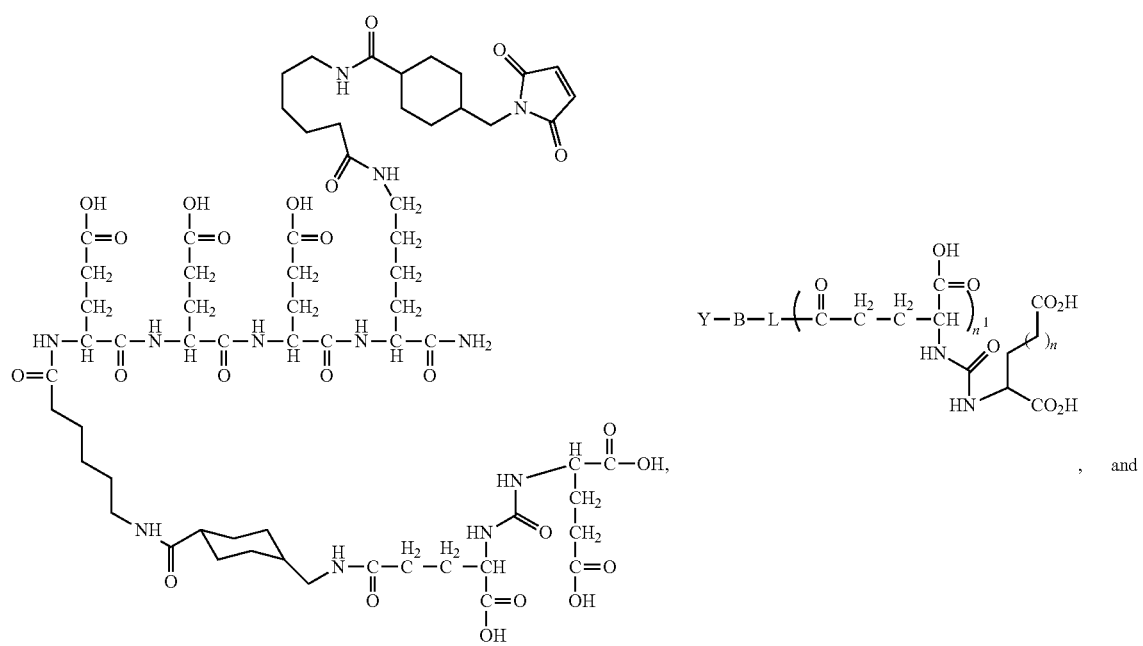
, and -continued

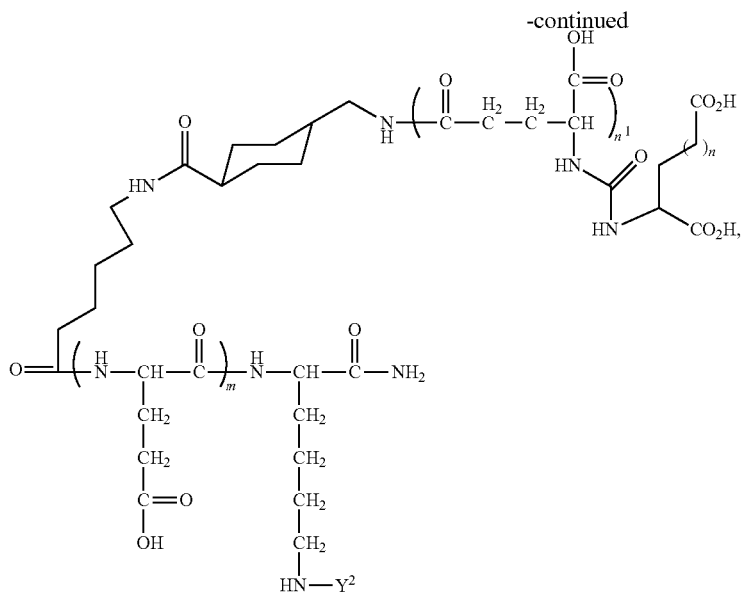

wherein m, n and $n^1$ are each independently 1, 2, 3, or 4;
L is an optionally substituted aliphatic or heteroaliphatic linking group;
B comprises at least one negatively charged amino acid, and
Y and $Y^2$ are the phthalocyanine compound of formula (I) that is directly or indirectly linked or coupled to B;
$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;
$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$alkylthio, $C_{1-6}$hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof;
(b) detecting the PSMA-targeted phthalocyanine compound bound to and/or complexed with prostate cancer cells to determine the location and/or distribution of the prostate cancer cells in the subject;
(c) surgically resecting the prostate cancer in the subject, wherein the detected PSMA-targeted phthalocyanine compound bound to and/or complexed with the prostate cancer cells guide surgical resection of the prostate cancer; and
(d) irradiating the PSMA-targeted phthalocyanine compound bound to and/or complexed with residual prostate cancer cells in the subject following surgical resection.

16. The method of claim 15, wherein $R^1$-$R^{16}$ of the phthalocyanine compound are independently selected from the group consisting of hydrogen, halogen, nitro, cyano, hydroxyl, thiol, amino, and methyl.

17. The method of claim 15, the PSMA ligand comprising a PSMA-1 ligand.

18. The method of claim 15, wherein intra-operative imaging (IOI) of the PSMA-targeted phthalocyanine compound bound to and/or complexed with the cancer cells defines a tumor margin in the subject to guide surgical resection of the cancer.

19. The method of claim 15, the phthalocyanine compound having formula (II):

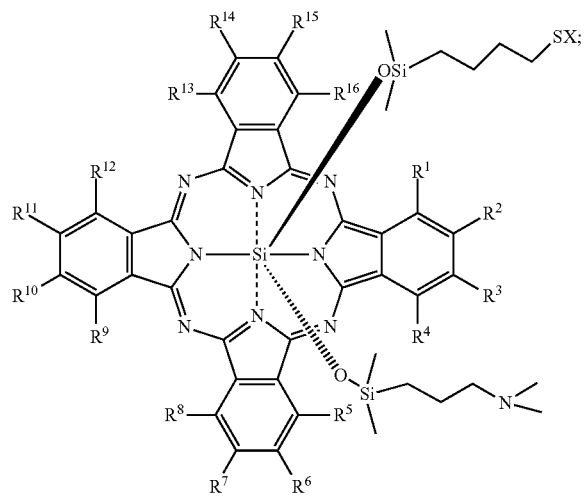

wherein X is a PSMA ligand selected from the group consisting of

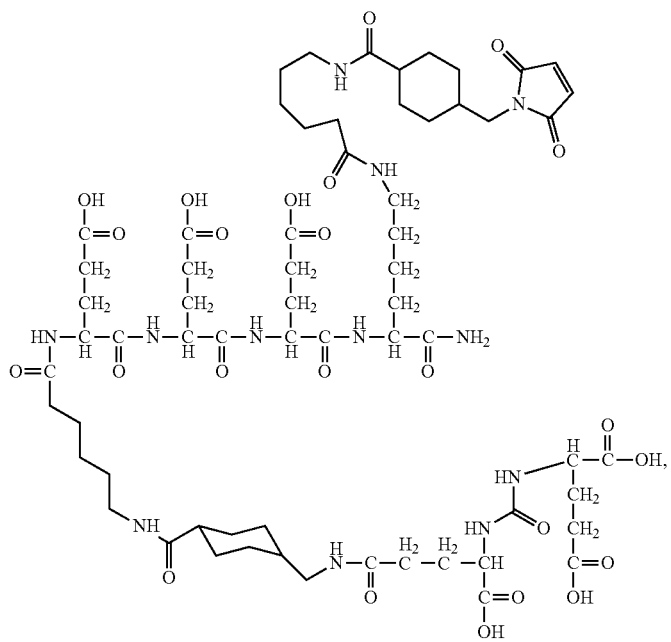
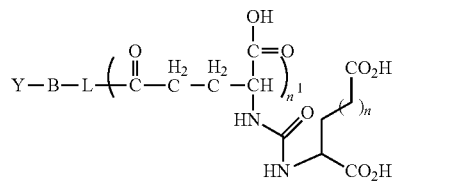
, and

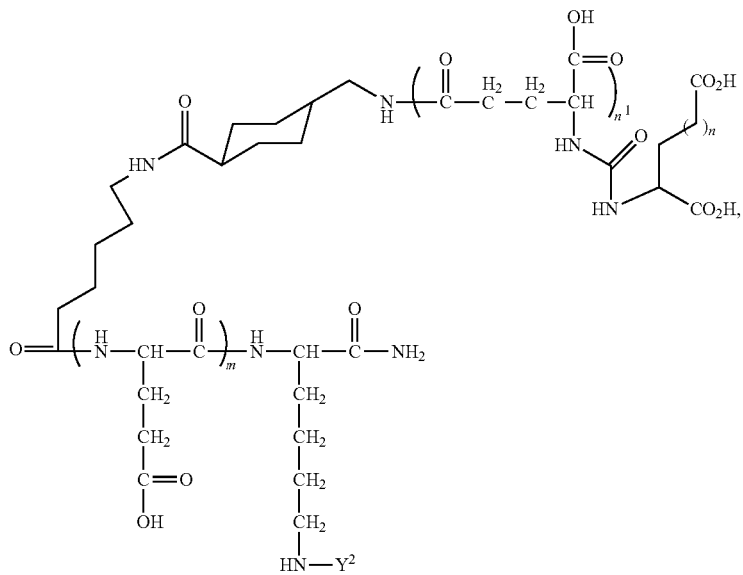

wherein m, n and $n^1$ are each independently 1, 2, 3, or 4;

L is an optionally substituted aliphatic or heteroaliphatic linking group;

B comprises at least one negatively charged amino acid, and

Y and $Y^2$ are the phthalocyanine compound of formula (I) that is directly or indirectly linked or coupled to B;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

20. The method of claim 19, wherein $R^1$-$R^{16}$ of the phthalocyanine compound are independently selected from the group consisting of hydrogen, halogen, nitro, cyano, hydroxyl, thiol, amino, and methyl.

21. The method of claim 15, the phthalocyanine compound having formula (III):
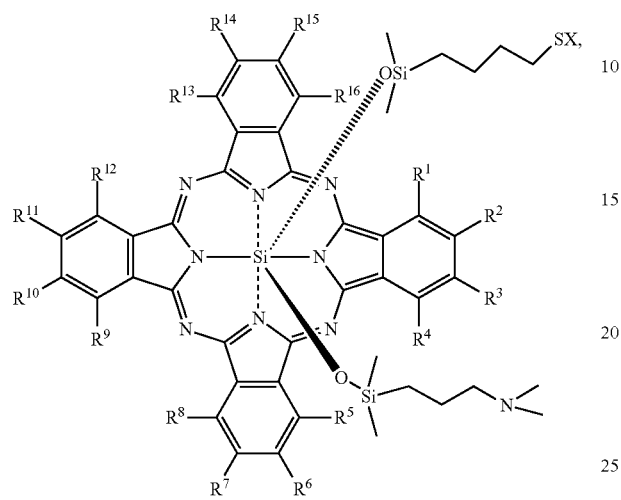
wherein X is a PSMA ligand selected from the group consisting of
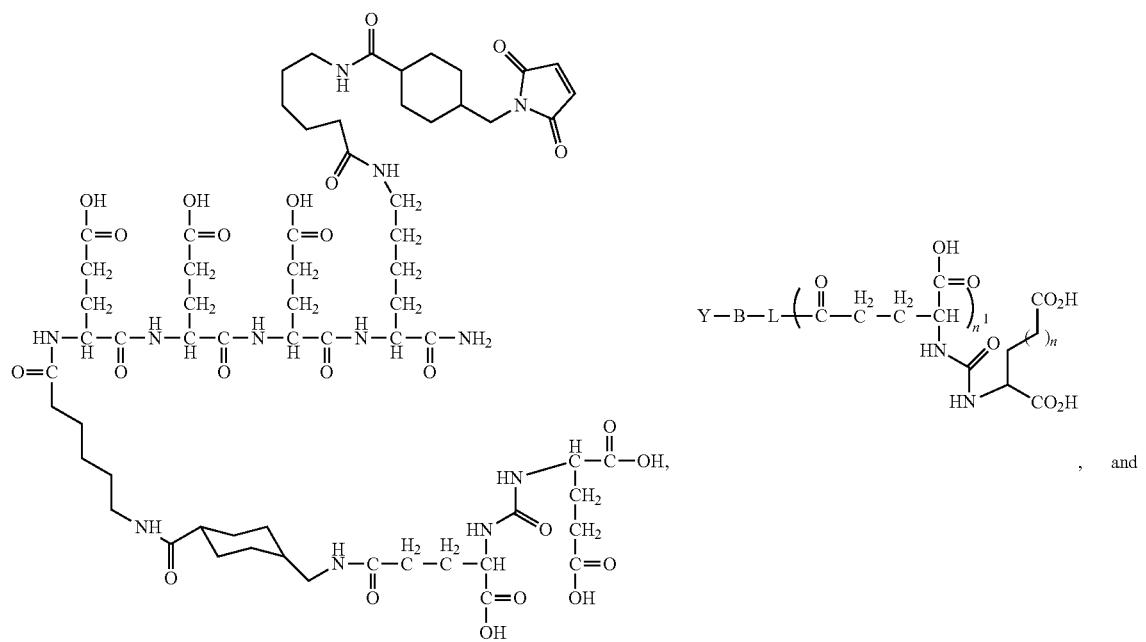
, and

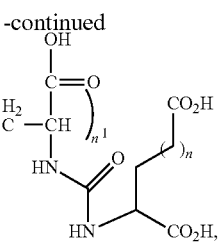
-continued

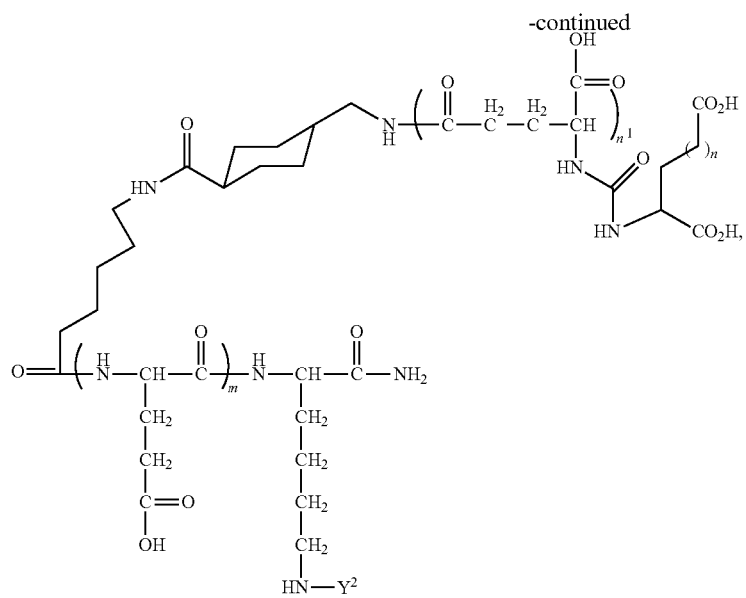

wherein m, n and $n^1$ are each independently 1, 2, 3, or 4;

L is an optionally substituted aliphatic or heteroaliphatic linking group;

B comprises at least one negatively charged amino acid, and

Y and $Y^2$ are the phthalocyanine compound of formula (I) that is directly or indirectly linked or coupled to B;

$R^1$, $R^4$, $R^5$, $R^8$, $R^9$, $R^{12}$, $R^{13}$, and $R^{16}$ are each independently selected from the group consisting of hydrogen, halogen, nitro, cyano, hydroxyl, thiol, amino, and methyl;

$R^2$, $R^3$, $R^6$, $R^7$, $R^{10}$, $R^{11}$, $R^{14}$, and $R^{15}$ are each independently selected from the group consisting of hydrogen, halogen, nitro, cyano, hydroxyl, thiol, amino, carboxy, aryl, heteroaryl, carbocyclyl, heterocyclyl, $C_{1-6}$ alkyl, $C_{1-6}$ alkenyl, $C_{1-6}$ alkynyl, $C_{1-6}$ alkoxy, $C_{1-6}$ acyl, $C_{1-6}$ alkylcarbonyloxy, $C_{1-6}$ carbocyclylalkyl, $C_{1-6}$ aminoalkyl, $C_{1-6}$ alkylamino, $C_{1-6}$ thioalkyl, $C_{1-6}$ alkylthio, $C_{1-6}$ hydroxyalkyl, $C_{1-6}$ alkyloxycarbonyl, $C_{1-6}$ alkylaminocarbonyl, and $C_{1-6}$ alkylcarbonylamino; and pharmaceutically acceptable salts thereof.

22. The method of claim 21, wherein $R^1$-$R^{16}$ of the phthalocyanine compound are independently selected from the group consisting of hydrogen, halogen, nitro, cyano, hydroxyl, thiol, amino, and methyl.

23. The method of claim 15, the phthalocyanine compound having formula (IV):

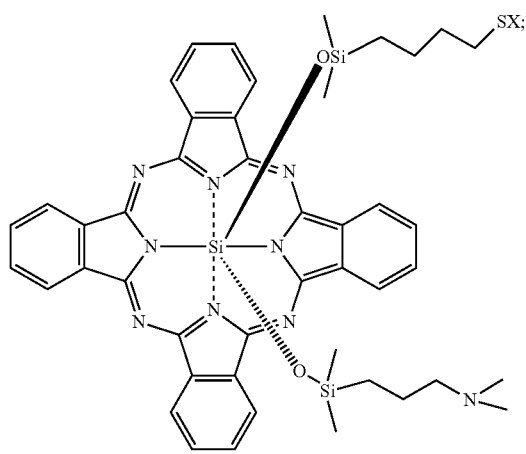

wherein X is a PSMA-1 ligand selected from the group consisting of

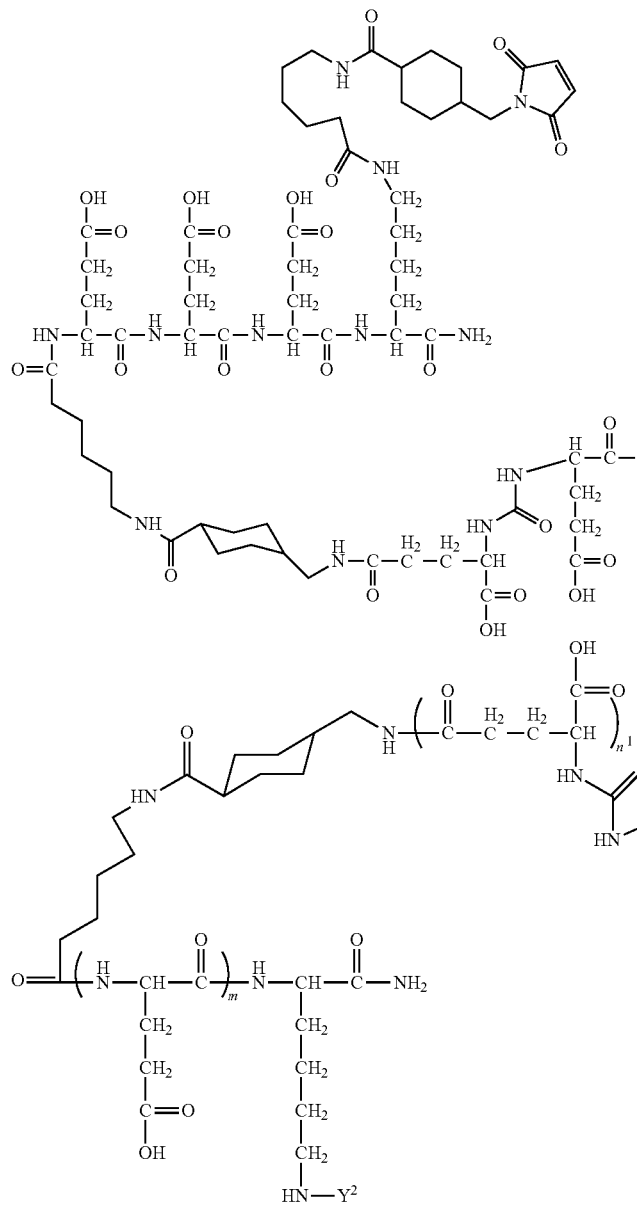
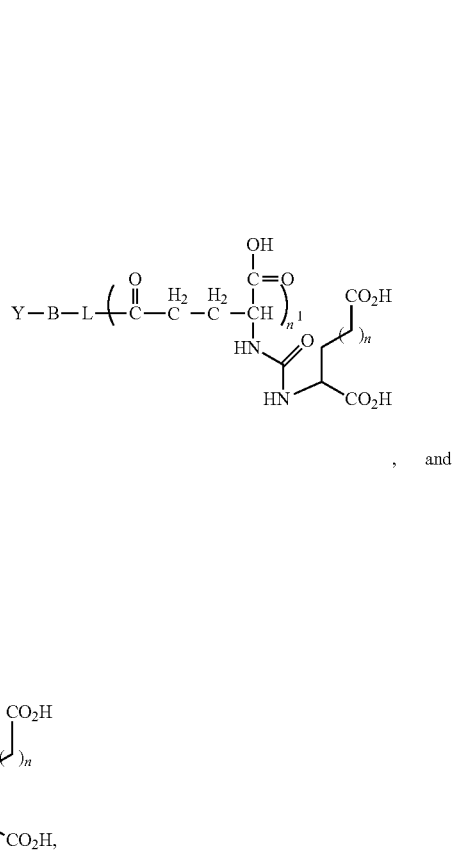
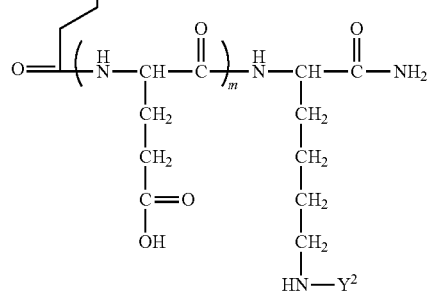

, and wherein m, n and $n^1$ are each independently 1, 2, 3, or 4;
L is an optionally substituted aliphatic or heteroaliphatic linking group;
B comprises at least one negatively charged amino acid, and
Y and $Y^2$ are the phthalocyanine compound of formula (I) that is directly or indirectly linked or coupled to B; and pharmaceutically acceptable salts thereof.

24. The method of claim 15, wherein the PSMA targeted phthalocyanine compound is administered by intravenous injection.

25. The method of claim 15, wherein the PSMA targeted phthalocyanine compound is formulated in a pharmaceutically acceptable carrier.

26. The method of claim 15, wherein the cancer is PSMA expressing metastatic prostate cancer.

27. The method of claim 15, wherein the residual prostate cancer cells in the subject following surgical resection are irradiated with an amount of radiation effective to reduce tumor growth in the subject.

* * * * *